(12) United States Patent
Villamil et al.

(10) Patent No.: US 12,383,750 B2
(45) Date of Patent: Aug. 12, 2025

(54) FEEDTHROUGH WITH AN INTEGRATED CHARGING ANTENNA FOR AN ACTIVE IMPLANTABLE MEDICAL DEVICE

(71) Applicant: Greatbatch Ltd., Clarence, NY (US)

(72) Inventors: Luis Daniel Villamil, Montevideo (UY); Keith W. Seitz, Clarence Center, NY (US); Jonathan Calamel, Clarence, NY (US); Thomas Marzano, East Amherst, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 394 days.

(21) Appl. No.: 17/972,893

(22) Filed: Oct. 25, 2022

(65) Prior Publication Data

US 2023/0135610 A1 May 4, 2023

Related U.S. Application Data

(60) Provisional application No. 63/273,355, filed on Oct. 29, 2021.

(51) Int. Cl.
*A61N 1/375* (2006.01)
*H01R 13/52* (2006.01)

(52) U.S. Cl.
CPC ....... *A61N 1/3754* (2013.01); *H01R 13/5224* (2013.01)

(58) Field of Classification Search
None
See application file for complete search history.

(56) References Cited

U.S. PATENT DOCUMENTS

| | | | |
|---|---|---|---|
| 6,414,835 B1* | 7/2002 | Wolf | A61N 1/3754 361/306.3 |
| 7,122,891 B2 | 10/2006 | Dishongh et al. | |
| 7,405,698 B2 | 7/2008 | De | |
| 7,908,014 B2 | 3/2011 | Schulman et al. | |
| 9,387,332 B2* | 7/2016 | Zhao | A61N 1/37229 |
| 9,502,754 B2 | 11/2016 | Zhao et al. | |
| 10,758,735 B2 | 9/2020 | Lim et al. | |

(Continued)

OTHER PUBLICATIONS

European Extended Search, Application 22204821.7, dated Mar. 17, 2023.

*Primary Examiner* — Erica S Lee
(74) *Attorney, Agent, or Firm* — Michael F. Scalise

(57) ABSTRACT

An inductive charging antenna for charging the power source of an active implantable medical device (AIMD) is described. The charging antenna is supported on the body fluid side of the feedthrough insulator, on the device side of the insulator or it is embedded inside the insulator. The charging antenna is connected to electronic circuits housed inside the medical device to charge the power source so that the device can deliver electrical stimulation to a patient and receive sensed biological signals from body tissue, among other functionalities. If the charging antenna is supported on the insulator body fluid side, it is made from a biocompatible material such as platinum. However, if the charging antenna is embedded inside the feedthrough insulator or is supported on the device side of the insulator, it can be made from a less expensive material that is not biocompatible, for example, copper.

20 Claims, 22 Drawing Sheets

(56) References Cited

U.S. PATENT DOCUMENTS

| | | |
|---|---|---|
| 11,005,156 B2 | 5/2021 | Ying |
| 2008/0021522 A1* | 1/2008 | Verhoef .................. H01Q 7/00 |
| | | 607/60 |
| 2008/0103558 A1 | 5/2008 | Wenzel et al. |
| 2008/0195180 A1* | 8/2008 | Stevenson ............... A61N 1/05 |
| | | 607/60 |
| 2009/0228074 A1* | 9/2009 | Edgell ...................... H01Q 1/40 |
| | | 607/60 |
| 2010/0109958 A1 | 5/2010 | Haubrich et al. |
| 2010/0109966 A1 | 5/2010 | Mateychuk et al. |
| 2010/0114245 A1 | 5/2010 | Yamamoto et al. |
| 2010/0114246 A1 | 5/2010 | Hill et al. |
| 2010/0168817 A1* | 7/2010 | Yamamoto ......... A61N 1/37229 |
| | | 607/60 |
| 2010/0168818 A1 | 7/2010 | Barror et al. |
| 2016/0087331 A1* | 3/2016 | Heppell ................... H04B 5/79 |
| | | 343/702 |
| 2019/0244729 A1* | 8/2019 | Seitz .................. C04B 41/4578 |
| 2022/0395692 A1* | 12/2022 | Primavera ............ A61N 1/3754 |

\* cited by examiner

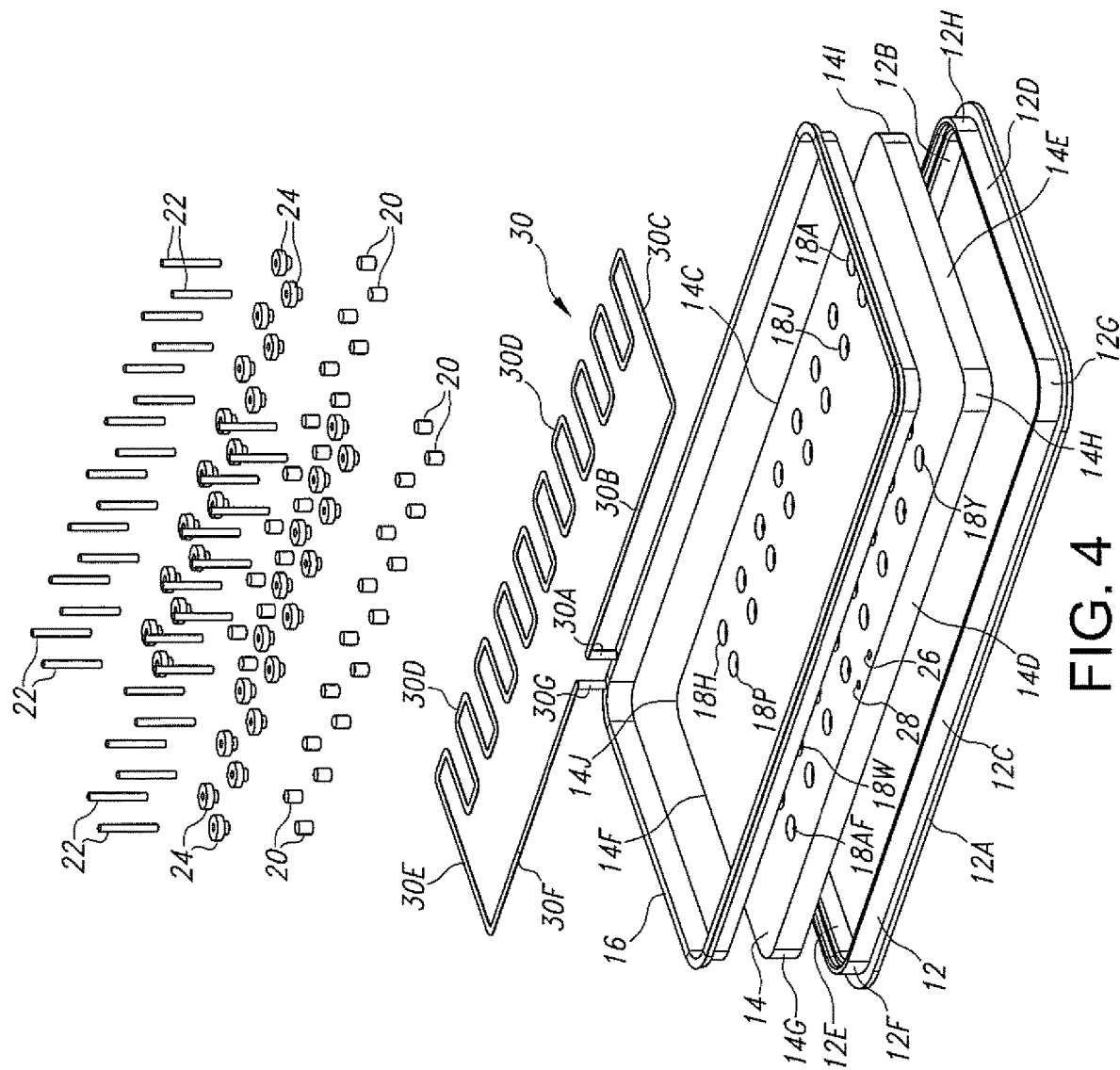

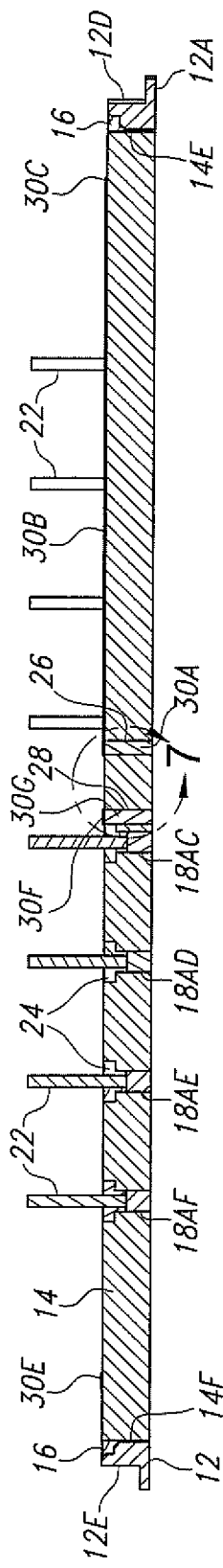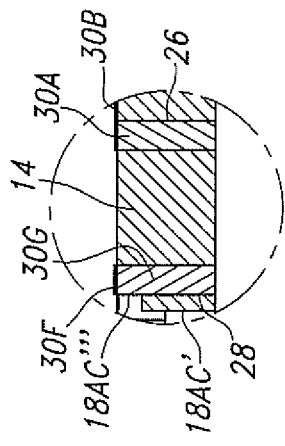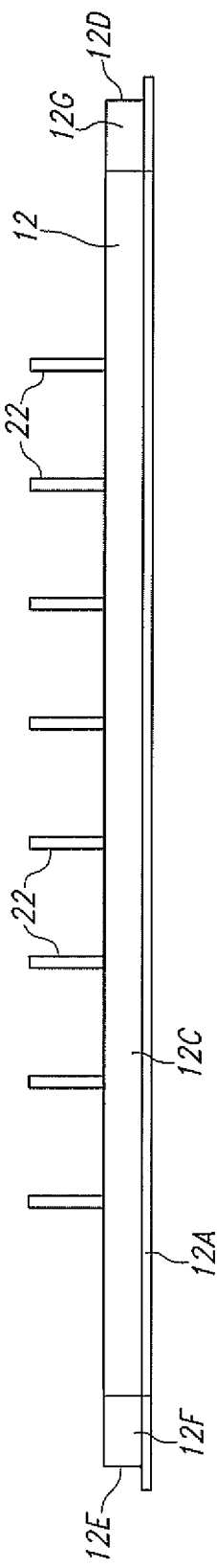

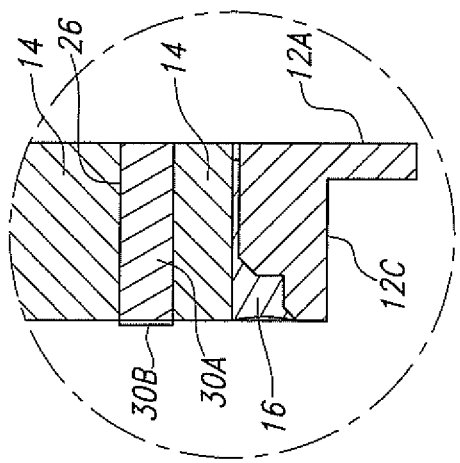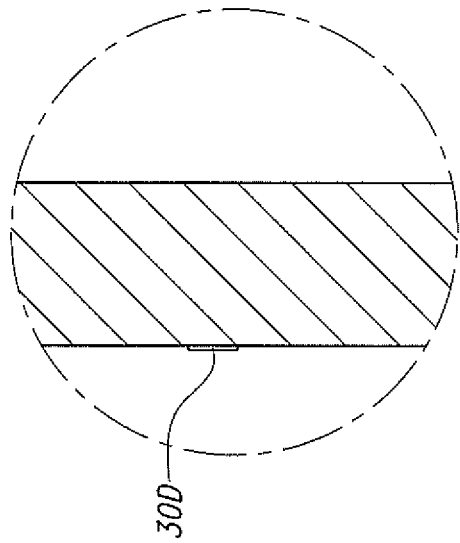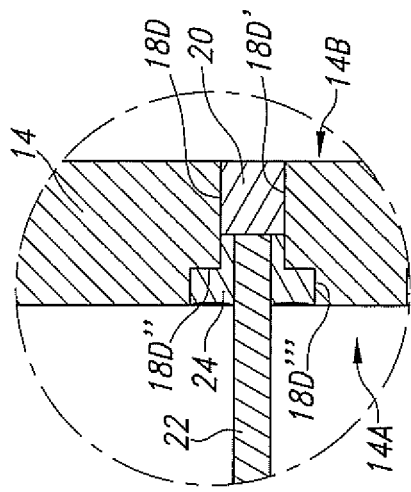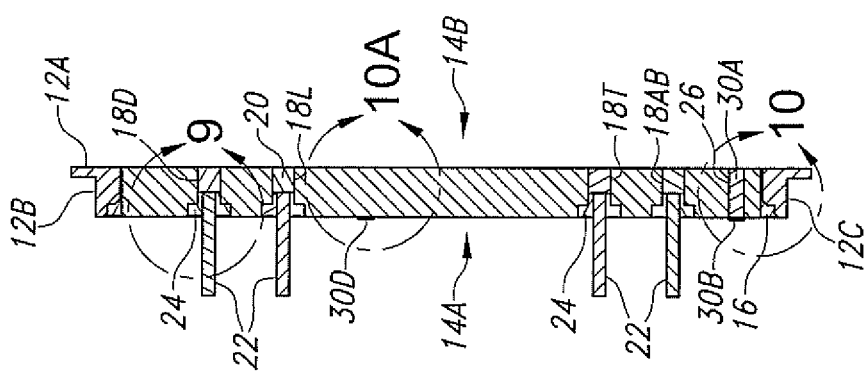

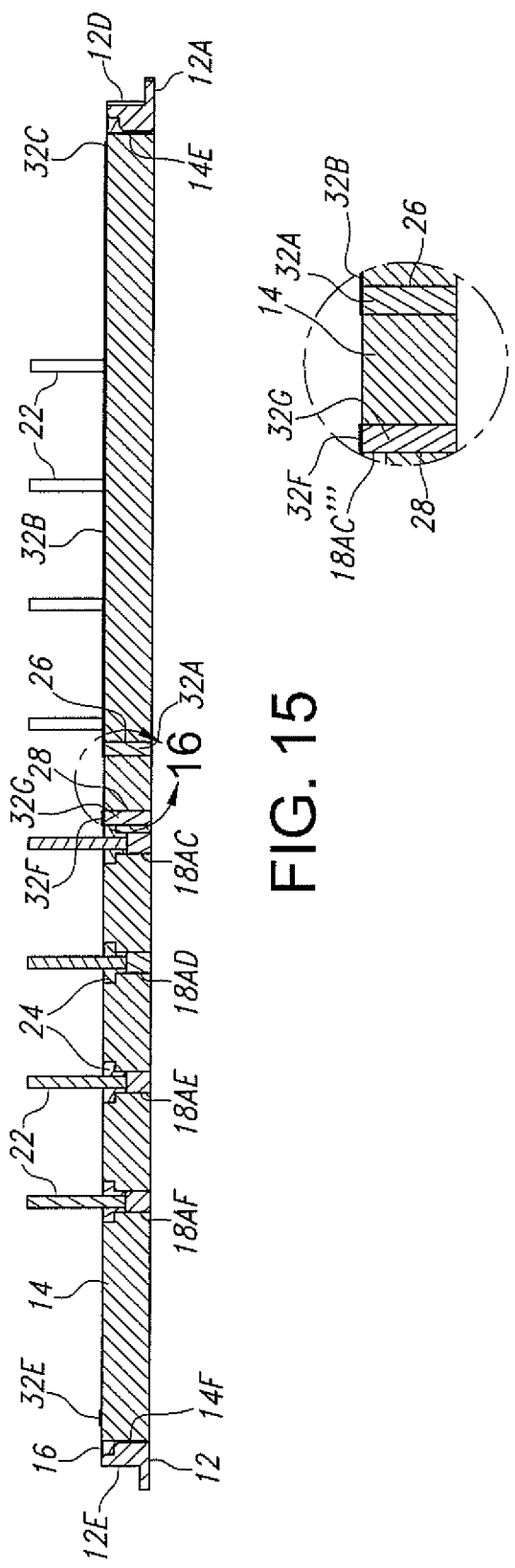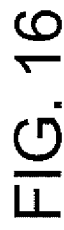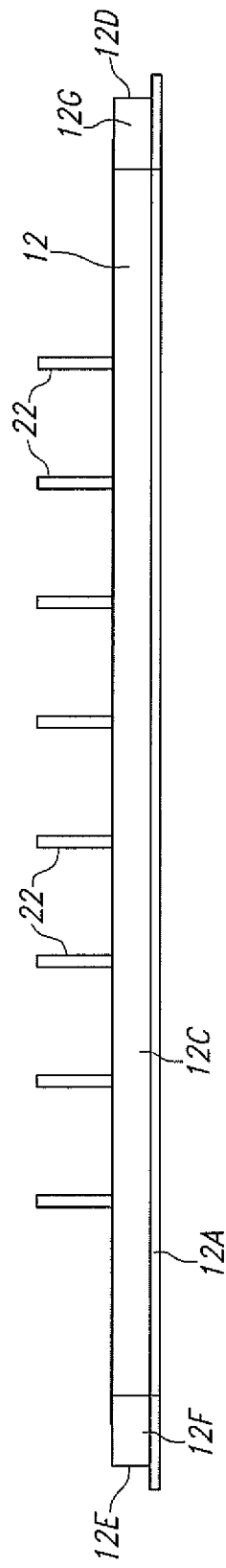
FIG. 15
FIG. 16
FIG. 14

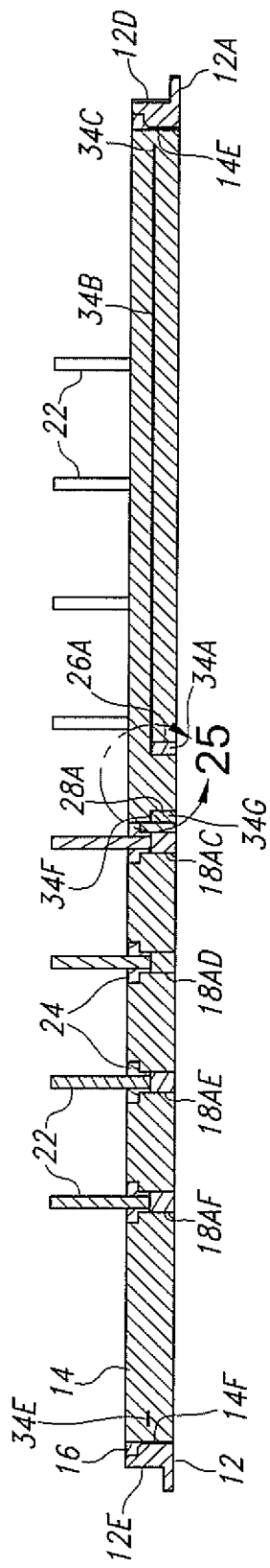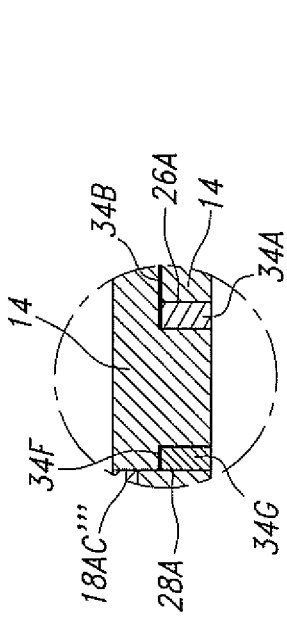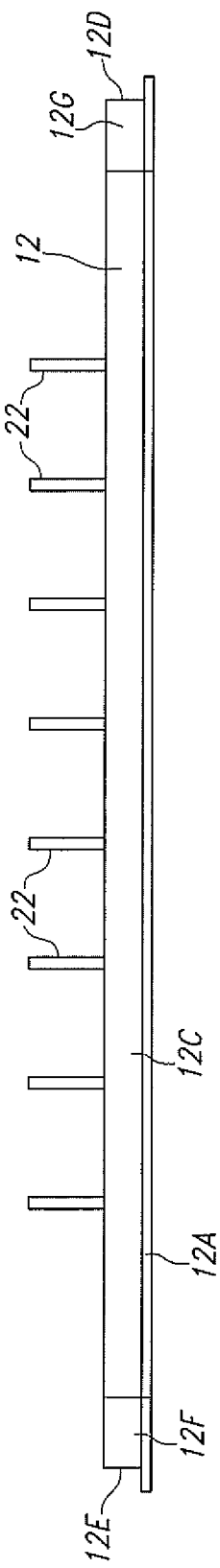

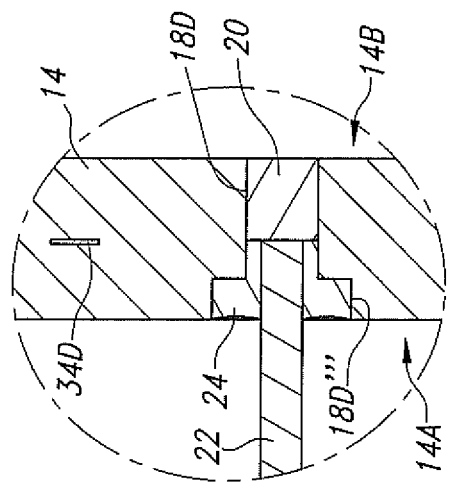
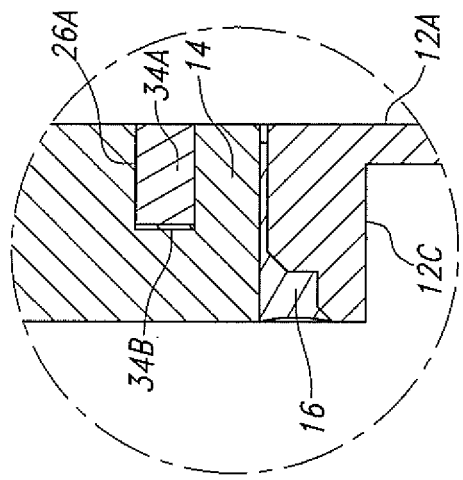
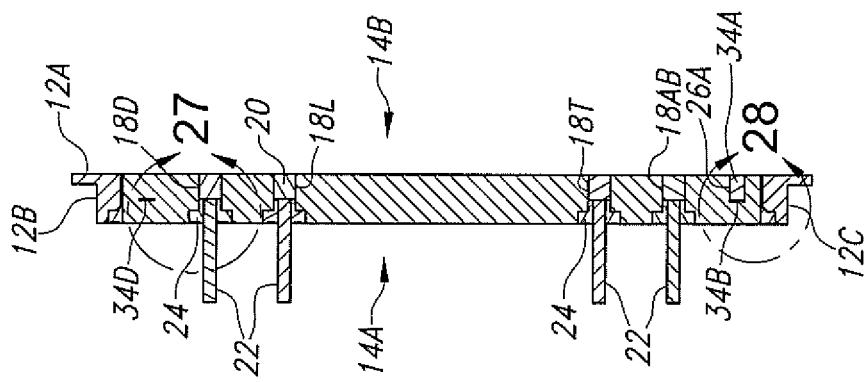

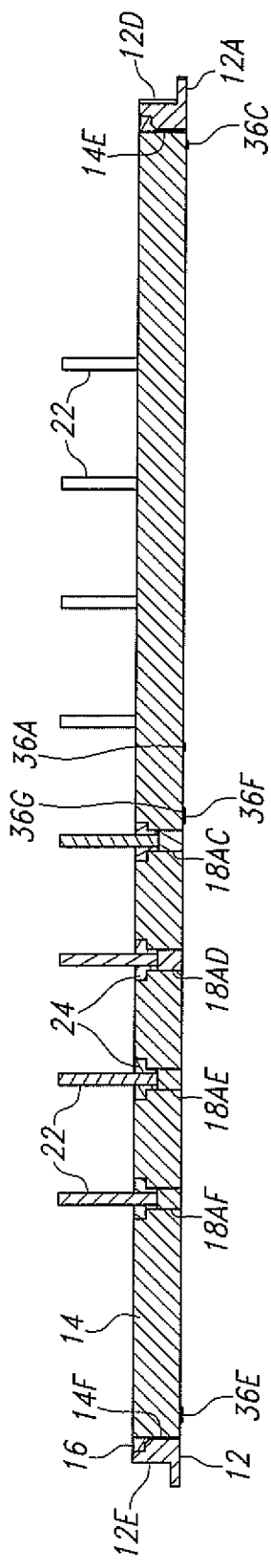
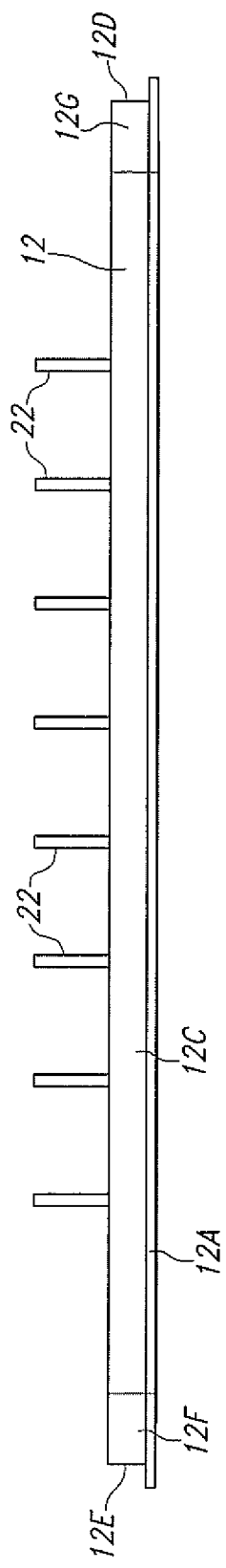

FEEDTHROUGH WITH AN INTEGRATED CHARGING ANTENNA FOR AN ACTIVE IMPLANTABLE MEDICAL DEVICE

CROSS-REFERENCE TO RELATED APPLICATION

This application claims priority to U.S. Provisional Application Ser. No. 63/273,355, filed on Oct. 29, 2021.

BACKGROUND OF THE INVENTION

1. Field of the Invention

The present invention relates to the field of medical devices, particularly implantable medical devices. Still more particularly, the present invention relates to a battery- or capacitor-powered active implantable medical device (AIMD) that is designed to deliver electrical stimulation to a patient or to sense biological signals from body tissue. The AIMD of the present invention has a charging antenna that is supported on the insulator for the terminal pin feedthrough. A preferred embodiment has the charging antenna formed of a biocompatible material such as platinum supported on the body fluid side of the feedthrough insulator.

2. Prior Art

The charging antenna for a medical device, for example, an active implantable medical device (AIMD) typically resides in the device header. This means that the charging antenna requires space in the header in addition to space that is allocated to terminal blocks. As is well known by those skilled in the art, the header terminal blocks are individually electrically connected to a terminal pin that is electrically isolated from the device housing by a feedthrough. The proximal end of the terminal pin is connected to electronic circuits inside the medical device housing while the terminal pin distal end is connected to a terminal block residing in the device header.

When a charging antenna is also housed in the header, the antenna requires space in addition to that which is required for the terminal blocks and associated electrical connections to the terminal pins. This additional space in the header typically includes a mechanical frame to support the antenna in its intended shape and position as well as space that is needed to accommodate the charging antenna assembly process. The assembly process includes supporting the charging antenna on its support frame and connecting the antenna to a feedthrough terminal pin.

Therefore, there is a desire to reduce the size of a medical device, such as an AIMD, by lessening the amount of space that is needed in the header for the charging antenna. Preferably, the charging antenna is completely removed from the header without adversely affecting its charging functionality.

SUMMARY OF THE INVENTION

As medical device technologies continue to evolve, active implantable medical devices (AIMD) have gained increased popularity in the medical field. An AIMD is a battery- or capacitor-powered device that is designed to deliver electrical stimulation to a patient or sense biological signals from the patient. To enable an AIMD to stay inside the patient's body for many years without needing to be replaced, an inductive charging antenna is connected to the capacitor or battery powering the medical device. However, in order to make medical devices and particularly implantable medical devices as small as possible, there is a desire to free up space in the header that is occupied by the charging antenna. In the present invention, the charging antenna is completely removed from the device header. Instead, the charging antenna is supported on the feedthrough insulator.

In that respect, the present invention describes several embodiments where the charging antenna is supported on the body fluid side of the feedthrough insulator, on the device side of the insulator and embedded inside the insulator between the body fluid and device sides. If the antenna is supported on the body fluid side, it must be made from a biocompatible material such as platinum. However, if the charging antenna is embedded inside the feedthrough insulator or is supported on the device side of the insulator, it can be made from a less expensive material that is not biocompatible, for example, copper.

These and other aspects of the present invention will become increasingly more apparent to those skilled in the art by reference to the following detailed description and to the appended drawings.

BRIEF DESCRIPTION OF THE DRAWINGS

FIG. 4 is an exploded view of the feedthrough 10 shown in FIG. 3.

FIG. 5 is a side elevational view of the feedthrough 10 shown in FIG. 3.

FIG. 6 is a cross-sectional view taken along line 6-6 of FIG. 3.

FIG. 7 is an enlarged view of the indicated section of FIG. 6.

FIG. 8 is a cross-sectional view taken along line 8-8 of FIG. 3.

FIG. 9 is an enlarged view of the indicated section of FIG. 8.

FIG. 10 is an enlarged view of the indicated section of FIG. 8.

FIG. 10A is an enlarged view of the indicated section of FIG. 8.

FIG. 14 is a side elevational view of the feedthrough 10A shown in FIG. 12.

FIG. 15 is a cross-sectional view taken along line 15-15 of FIG. 12.

FIG. 16 is an enlarged view of the indicated section of FIG. 15.

FIG. 23 is a side elevational view of the feedthrough 10B shown in FIG. 21.

FIG. 24 is a cross-sectional view taken along line 24-24 of FIG. 21.

FIG. 25 is an enlarged view of the indicated section of FIG. 24.

FIG. 26 is a cross-sectional view taken along line 26-26 of FIG. 21.

FIG. 27 is an enlarged view of the indicated section of FIG. 26.

FIG. 28 is an enlarged view of the indicated section of FIG. 26.

FIG. 32 is a side elevational view of the feedthrough 10C shown in FIG. 30.

FIG. 33 is a cross-sectional view taken along line 33-33 of FIG. 30.

DETAILED DESCRIPTION OF THE PREFERRED EMBODIMENTS

Figure 1:
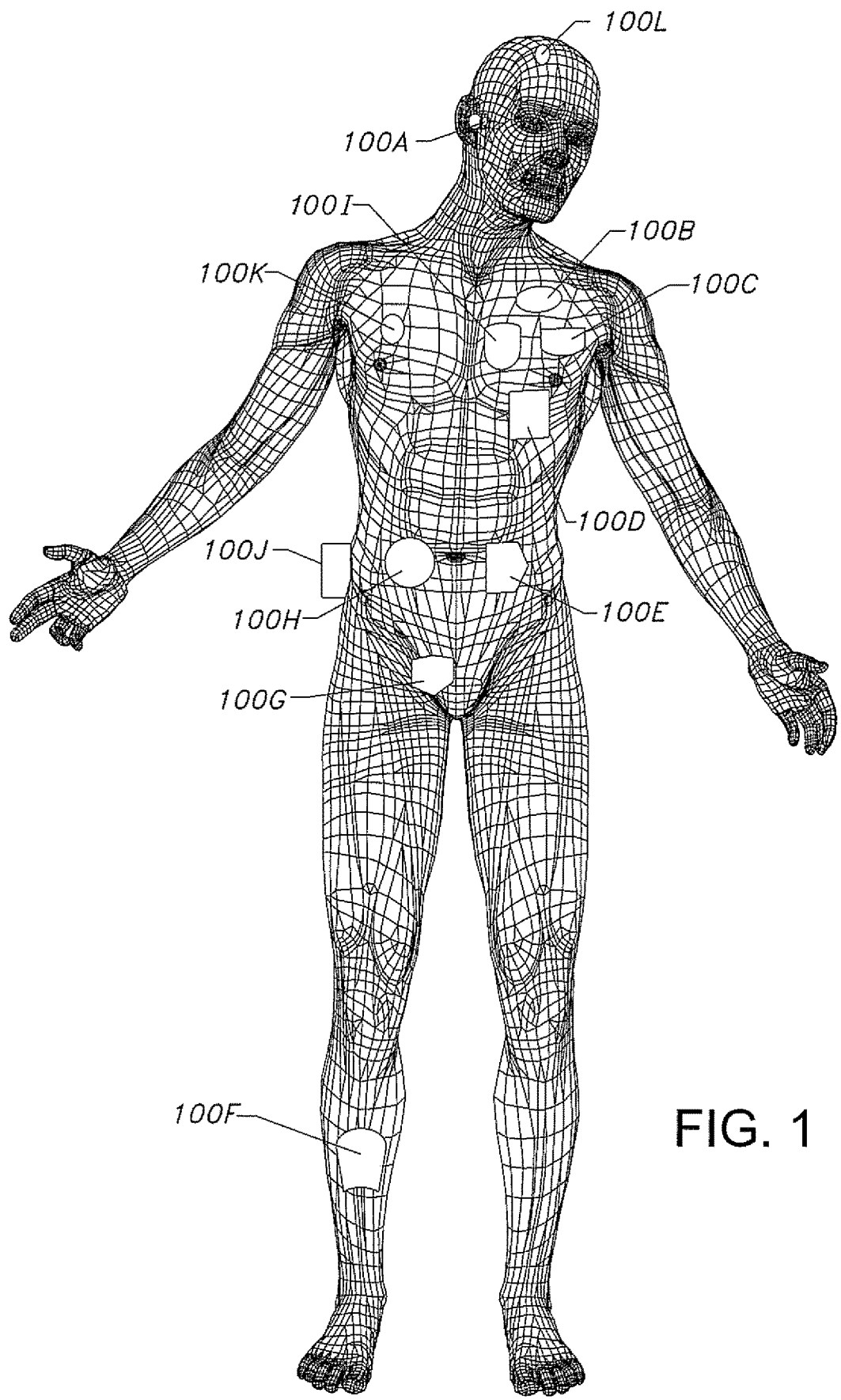
FIG. 1 is a wire formed diagram of a generic human body showing a number of medical devices 100A to 100L that can either be implanted in a patient's body tissue or attached externally to the body.

Turning now to the drawings, FIG. 1 is a wire formed diagram of a generic human body illustrating various types of active implantable and external medical devices 100 that can either be implanted in a patient's body tissue or attached externally to the body.

Numerical designation 100A represents a family of hearing devices which can include the group of cochlear implants, piezoelectric sound bridge transducers, and the like.

Numerical designation 100B represents a variety of neurostimulators and brain stimulators. Neurostimulators are used to stimulate the Vagus nerve, for example, to treat epilepsy, obesity, and depression. Brain stimulators are pacemaker-like devices and include electrodes implanted deep into the brain for sensing the onset of a seizure and also providing electrical stimulation to brain tissue to prevent a seizure from actually occurring. The lead wires associated with a deep brain stimulator are often placed using real time MRI imaging.

Numerical designation 100C shows a cardiac pacemaker which is well-known in the art.

Numerical designation 100D includes the family of left ventricular assist devices (LVADs), and artificial heart devices.

Numerical designation 100E includes a family of drug pumps which can be used for dispensing insulin, chemotherapy drugs, pain medications and the like.

Numerical designation 100F includes a variety of bone growth stimulators for rapid healing of fractures.

Numerical designation 100G includes urinary incontinence devices.

Numerical designation 100H includes the family of pain relief spinal cord stimulators and anti-tremor stimulators.

Numerical designation 100H also includes an entire family of other types of neurostimulators used to block pain.

Numerical designation 100I includes a family of implantable cardioverter defibrillator (ICD) devices and also includes the family of congestive heart failure devices (CHF). This is also known in the art as cardio resynchronization therapy devices, otherwise known as CRT devices.

Numerical designation 100J illustrates an externally worn pack. This pack could be an external insulin pump, an external drug pump, an external neurostimulator or even a ventricular assist device.

Numerical designation 100K illustrates one of various types of EKG/ECG external skin electrodes which can be placed at various locations.

Numerical designation 100L represents external EEG electrodes that are placed on the head.

Figure 2:
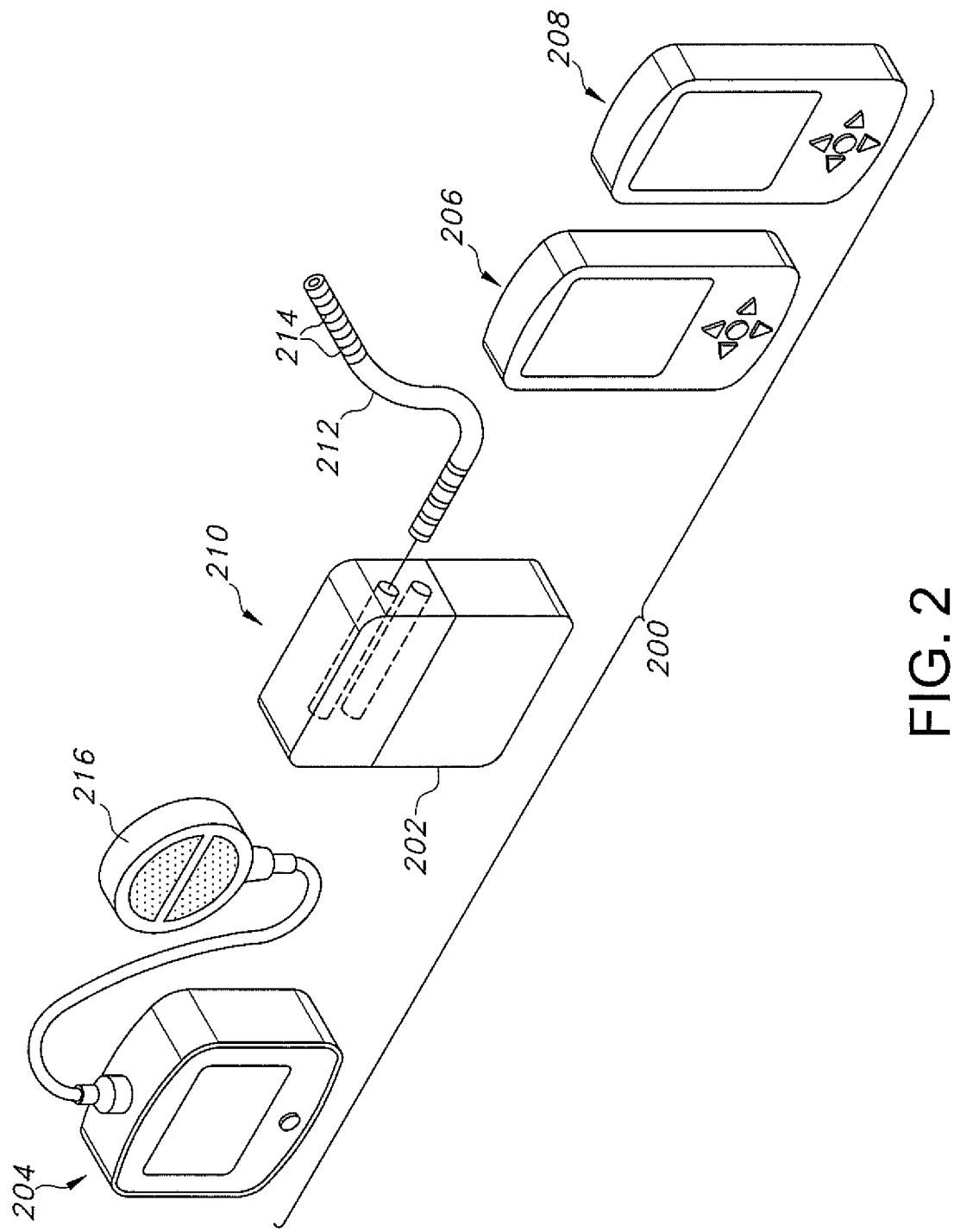
FIG. 2 is a simplified block diagram of an exemplary medical system 10 according to various embodiments of the present invention.

To provide context to the various medical devices 100A to 100L illustrated in FIG. 1, FIG. 2 illustrates a simplified block diagram of an exemplary medical system 200 according to the present invention. The medical system 200 includes a medical device 202, which can be one of the exemplary medical devices 100A to 100L depicted in FIG. 1, an external charger 204, a patient programmer 206, and a clinician programmer 208. The exemplary medical device 202 may be an active implantable medical device (AIMD) 210, which can be implanted in a patient's body. In some embodiments, the AIMD 210 is coupled to one end of an implantable lead 212. The other end of the lead 212 includes multiple electrodes 214 through which electrical current is applied to a desired part of the body tissue of a patient. The implantable lead 214 incorporates electrical conductors to provide a path for that current to travel to the body tissue from the AIMD 210. Although only one implanted lead 212 is shown in FIG. 2, it is understood that a plurality of implanted leads may be attached to the AIMD 210. Furthermore, the type of implanted lead that may be used in the medical system 200 is not limited to the embodiment shown in FIG. 2. For example, a paddle lead may be implemented in certain embodiments.

The patient programmer 206 and the clinician programmer 208 may be portable handheld devices, such as a smartphone or other custom device, that are used to configure the AIMD 210 so that the AIMD can operate in a desired manner. The patient programmer 206 is used by the patient in whom the AIMD 210 is implanted. The patient may adjust the parameters of electrical stimulation delivered by the AIMD 210, such as by selecting a stimulation program, changing the amplitude and frequency of the electrical stimulation, and other parameters, and by turning stimulation on and off.

The clinician programmer 208 is used by medical personnel to configure the other system components and to adjust stimulation parameters that the patient is not permitted to control, such as setting up stimulation programs among which the patient may choose and setting upper and lower limits for the patient's adjustments of amplitude, frequency, and other parameters. It is also understood that although FIG. 2 illustrates the patient programmer 206 and the clinician programmer 208 as two separate devices, they may be integrated into a single programmer in some embodiments.

Figure 3:
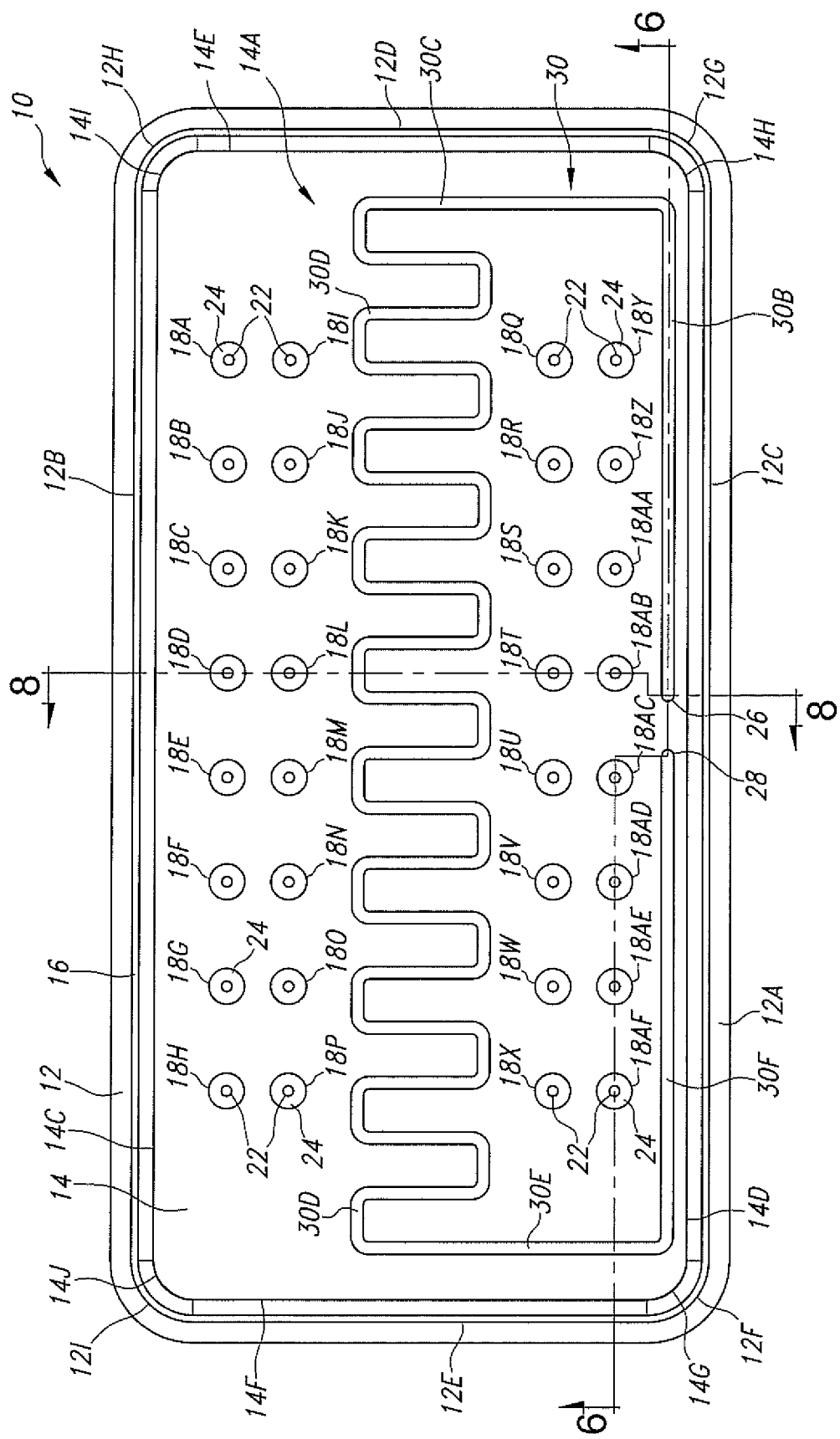
FIG. 3 is a plan view looking at the body fluid side of a feedthrough 10 according to the present invention.
Figure 11:
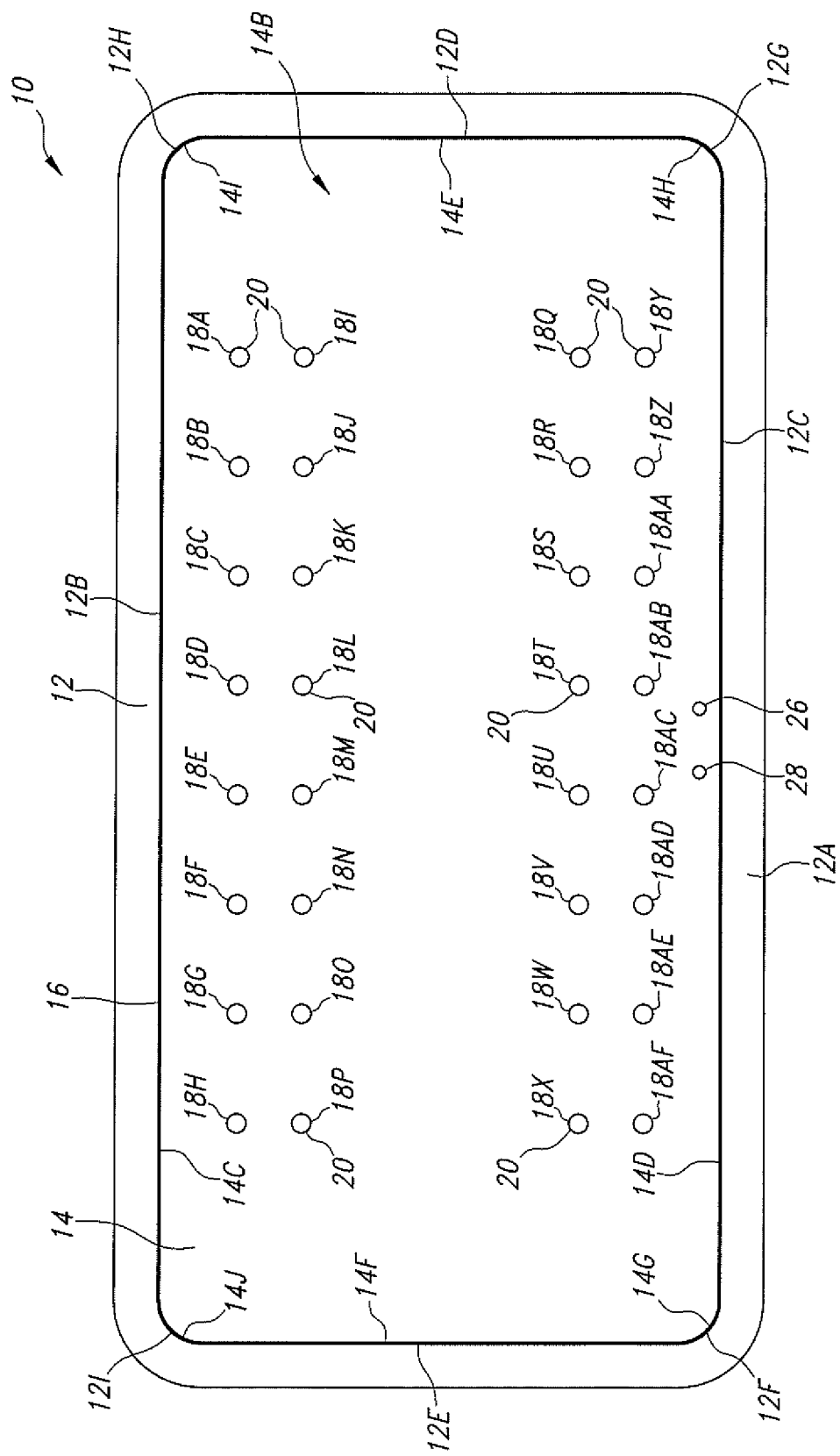
FIG. 11 is a plan view looking at the device side of the feedthrough 10 shown in FIG. 3.

Referring now to FIGS. 3 to 11, a first embodiment of a feedthrough 10 according to the present invention is illustrated. The feedthrough 10 comprises a ferrule 12 supporting a ceramic insulator 14. The insulator 14 resides in an opening in the ferrule 12 and is hermetically sealed to the ferrule by a ring-shaped braze 16. FIGS. 3 and 11 are plan views looking at the body fluid side surface and the device side surface, respectively, of the insulator 14 and FIG. 4 is an exploded view of the feedthrough 10.

The ferrule 12 comprises a surrounding sidewall that is integrally connected to an outwardly extending flange 12A. When the ferrule 12 is sealed in an opening in the housing for an active implantable medical device, for example the AIMD 210 shown in FIG. 2, the flange 12A is welded to the device housing with the flange edge providing an esthetically contoured transition from the ferrule 12 to the device housing.

The ferrule sidewall has a generally rectangular shape formed by opposed ferrule long sides 12B and 12C that extend to and meet with opposed ferrule short ends 12D and 12E at curved corners. More particularly, end 12E meets side 12C at curved corner 12F, side 12C meets end 12D at curved corner 12G, end 12D meets side 12B at curved corner 12H, and side 12B meets end 12E at a curved corner 12I.

The feedthrough insulator 14 is formed from a unitary body of ceramic material in a green-state or it is formed from a plurality of green-state ceramic sheets that are stacked one upon another until a desired thickness is obtained. In any event, the green-state body or laminated green-state ceramic sheets are then subjected to a sintering process to form a unitary ceramic insulator 14 of a desired shape. Sintering a green-state ceramic material is well known to those skilled in the art.

A suitable material for the insulator 14 is a ceramic, for example, essentially high purity alumina of the chemical formula $Al_2O_3$ or 3% YSZ. "Essentially pure" means that the post-sintered ceramic is at least 96% alumina up to 99.999% alumina. In various embodiments, the post-sintered ceramic container 12 is at least 90% alumina, preferably at least 92% alumina, more preferably at least 94% alumina, and still more preferably at least 96% alumina. Other materials that are suitable for the insulator are selected from zirconia, sapphire, aluminum nitride, alumina toughened zirconia, boron nitride, ceramic-on-ceramic, partially stabilized zirconia, strontium aluminate, yttria-stabilized zirconia, zirconia toughened alumina, zirconia toughened ceramics, celsian ($BaAl_2Si_2O_8$), borosilicate sealing glasses, compression sealing glasses, a $Li_2O \times Al_2O_3 \times nSiO_2$ glass-ceramic system (LAS system), a $MgO \times Al_2O_3 \times nSiO_2$ glass-ceramic system (MAS system), a $ZnO \times Al_2O_3 \times nSiO_2$ glass-ceramic system (ZAS system), and combinations thereof.

The sintered insulator 14 comprises a surrounding sidewall extending to an insulator body fluid side surface 14A and an insulator device side surface 14B. The insulator sidewall has a shape that substantially matches that of the ferrule 12 except the sidewall has shorter sides and ends so that the insulator fits into an opening bounded by the surrounding sidewall of the ferrule 12. In that manner, the insulator sidewall has a generally rectangular shape formed by opposed insulator long sides 14C and 14D that extend to and meet with opposed insulator short ends 14E and 14F at curved corners. More particularly, end 14F meets side 14D at curved corner 14G, side 14D meets end 14E at curved corner 14H, end 14E meets side 14C at curved corner 14I, and side 14C meets end 14F at curved corner 14J.

A ring-shaped braze 16, preferably a gold braze, resides between, and hermetically seals the ferrule 12 to the insulator 14. However, as is well known by those skilled in the art, before the insulator 14 is brazed to the ferrule 12, the insulator sidewall is provided with a metallization (not shown) so that the braze wets to the insulator. The metallization typically comprises two metallization layers, a first adhesion layer that is directly applied to the outer surface of the insulator surrounding sidewall, and a second, wetting layer, which is applied on top of the adhesion layer. In a preferred embodiment, the adhesion layer is titanium, and the wetting layer is either molybdenum or niobium.

The adhesion and wetting metallization layers may be applied to the insulator sidewall by thin and thick film technologies, such as printing, painting, plating, and deposition processes. Metallization processes include screen printing, pad printing, brush coating, direct bonding, active metal brazing, magnetron sputtering, physical vapor deposition, ion implantation, electroplating, and electroless plating. In an alternate embodiment, both the adhesion and wetting metallization layers may be provided by a single metallization layer. It is noted that in the present drawings, the adhesion and wetting layers are intentionally not shown for the sake of simplicity, however, it is understood that perimeter metallizations are present for each of the ceramic feedthrough insulators according to the present invention. Further, every one of the vias extending through the feedthrough insulators is provided with a suitable metallization.

Moreover, while the insulator 14 hermetically sealed to the ferrule 12 are shown having matching generally rectangular shapes, that is by way of example only. Those skilled in the art will readily understand that the insulator 14 hermetically sealed to the ferrule 12 by braze 16 can have a myriad of different shapes that are limited only by the design requirements of the implantable device to which the feedthrough 10 is intended to be connected.

A plurality of vias 18A to 18AF extend through the thickness of the insulator 14 from the insulator body fluid side surface 14A to the insulator device side surface 14B. FIGS. 8 and 9 show via 18D as a representative or exemplary one of the vias 18A to 18AF. Via 18D has a device side portion 18D' of a first diameter that extends from the device side surface 14B of the insulator 14 to an annular step 18D". At the step 180", the via 18D widens to a body fluid side portion 180'" having a second diameter that is greater than the first diameter. The body fluid side portion 18D'" of the via 18D extends to the body fluid side surface 14A of the insulator 14. The other vias 18A to 18C and 18E to 18AF are similarly constructed; they each have a step delineating a body fluid side portion from a device side portion.

The vias 18A to 18AF are arranged in four rows of eight vias. As shown, the first row includes vias 18A to 18H, the second row includes vias 18I to 18P, the third row includes vias 18Q to 18X, and the fourth rows includes vias 18Y to 18AF. It is understood, however, that the arrangement of the vias in four rows of eight is exemplary. There can be a lesser or greater number of vies than that which is shown, and the vias can be provided in any of a myriad of different arrangements that are specific to an intended use of the feedthrough 10. The vias 18A to 18AF are preferably formed by drilling, punching, cutting, machining, and waterjet cutting through the insulator 14.

As shown in FIGS. 4, 8 and 9, each via 18A to 18AF supports an electrically conductive material 20 and, preferably an electrically conductive platinum-containing material, that is hermetically sealed to the insulator 14 in a major portion of a device side portion (portion 18D' for via 18D) of the via. The conductive material 20 does not extend to the step (step 18D" for via 18D) and is comprised of a platinum-containing material, for example, a substantially closed pore, fritless and substantially pure platinum material that fills a major portion of the device side portion of each of the vias 18A to 18AF. The platinum-containing material 20 is hermetically sealed to the insulator 14 and has a leak rate that is not greater than $1 \times 10^{-7}$ std. cc He/sec.

In an exemplary embodiment of the present invention, the electrically conductive platinum-containing material is initially in the form of a paste or ink of a substantially pure platinum fill that is disposed within the major portion of a device side portion (portion 18D' for via 18D) of the via with the ceramic material of the insulator being in the green-state, as described above. Upon sintering the green-state ceramic material, whether the ceramic is a unitary body or a stack of ceramic sheets, the paste or ink of the platinum-containing material is co-sintered with the green-state ceramic to form a platinum-filled via portion with the platinum being hermetically sealed to the insulator without the aid of a metallization contacting the insulator in the via. A suitable process for forming a platinum-containing via in a ceramic substrate is described in U.S. Pat. No. 8,653,384 to Tang et al., which is assigned to the assignee of the present invention and incorporated herein by reference.

According to another embodiment of the present invention, in lieu of the substantially pure platinum material 20, the major portion of the device side portion (portion 18D' for via 18D) of each of the vias 18A to 18AF is filled with a composite reinforced metal ceramic (CRMC) material. The CRMC material is a platinum-containing material that comprises, by weight %, from about 10:90 ceramic:platinum to about 90:10 ceramic:platinum or, from about 70:30 ceramic:platinum to about 30:70 ceramic:platinum. The ceramic is preferably alumina.

As shown in FIGS. 3, 8 and 9, a terminal pin 22 extends through the body fluid side portion (portion 18D''' for via 18D) of each of the vias 18A to 18AF and into the device side portion (portion 18D' for via 18D) to abut the conductive material 20. The terminal pin 22 is hermetically secured in place in the body fluid side portion and part of the device side portion of each of the vias 18A to 18AF by a braze 24, preferably a gold braze 24. With the terminal pin 22 abutting the platinum-containing material 20, an electrically conductive pathway is established through each of the vias 18A to 18AF from the body fluid side surface 14A to the device side surface 14B of the insulator 14.

FIG. 11 illustrates that a pair of vias 26 and 28 are arranged side-by-side adjacent to side 140 of the insulator 14 and side 12C of the ferrule 12. These vias 26 and 28 are spaced from vias 18AB and 18AC.

Referring back to FIG. 3, an electrically conductive trace 30 serving as an inductive charging antenna is supported on the body fluid side surface 14A of the insulator. Since the antenna trace 30 will be exposed to body fluids, and the like, it must be a biocompatible material. Suitable biocompatible materials include platinum, platinum alloys, gold, gold alloys, rhodium, titanium, molybdenum, and mixtures thereof, and the antenna trace 30 may be applied to the insulator by thin and thick film technologies, such as printing, screen printing, pad printing, painting, plating, brush coating, direct bonding, active metal brazing, magnetron sputtering, physical vapor deposition, ion implantation, electroplating, and electroless plating.

The antenna trace 30 has a first leg portion 30A that is received in the via 26 where it is hermetically sealed to the insulator 14. The antenna trace 30 has a first lateral portion 30B that extends along the body fluid side surface 14A of the insulator from the first leg portion 30A and between the insulator side 14D and vias 18AB, 18AA, 18Z and 18Y to a curved turn spaced from the insulator end 14E. There, the first lateral portion 30B of the antenna trace 30 forms a second lateral portion 30C that extends about half-way along the length of but spaced from the insulator end 14E. A little more than half-way along the length of the insulator end 14E, the second lateral trace portion 30C curves toward the opposite insulator end 14F and forms into a rectangularly-shaped serpentine trace portion 30D extending along the body fluid side surface 14A between the second and third rows of vias 18I to 18P and 18Q to 18X. A short distance spaced from the end 14F of insulator 14, the rectangularly-shaped serpentine portion 30D of the antenna trace 30 makes a curved turn and forms into a third lateral trace portion 30D that extends along the body fluid side surface, spaced from the insulator side 14D. A short distance from the insulator side 14D, the third lateral trace portion 30D makes another curved turn and forms a fourth lateral trace portion 30F that extends between but spaced from vias 18AC to 18AF and the insulator side 14D to meet via 28. At via 28, the fourth lateral trace portion 30F forms a second leg portion 30G that resides in the via 28 where it is hermetically sealed to the insulator 14. The distal ends of the leg portions 30A and 30G reside at the device side surface 14B of the insulator 14 and are configured for subsequent electrical connection to electronic circuits (not shown) housed inside the AIMD 210.

The electronic circuits housed inside the medical device are configured to deliver electrical stimulation therapy to body tissue via an implantable lead, for example, the exemplary lead 212 shown in FIG. 2, connected to a terminal block (not shown) in the device header and to sense electrical biological signals from the body tissue through the same or a different implantable lead. Transmission of electrical stimulation therapy and sensed biological signals pass back and forth from the device electronic circuits to the exemplary lead electrodes 214 in contact with the body tissue. This transmission is along terminal pins that are supported in the feedthrough 10. In the various feedthrough embodiments according to the present invention, the electrically conductive material 20 contacting terminal pin 22 forms an electrically conductive pathway that is functionally equivalent to a terminal pin as a wire having a length that extends outwardly from both the body fluid and device side surfaces 14A, 14B of the insulator 14.

While the rectangularly-shaped serpentine portion 30D of the antenna trace 30 is shown extends between the second and third rows of vias 18I to 18P and 18Q to 18X, it is within the scope of the present invention that the antenna portion 30D can extend along the body fluid side surface 14A of the insulator 14 in a different pattern. For example, the rectangularly-shaped serpentine portion 30D can extends between the first and second rows of vias 18A to 18H and 18I to 18P, or between the third and fourth rows of vias 18Q to 18X and 18Y to 18AF. It can also extend between side 14C of the insulator and vias 18A to 18H or between the insulator side 14D and vias 18Y to 18AF.

Figure 12:
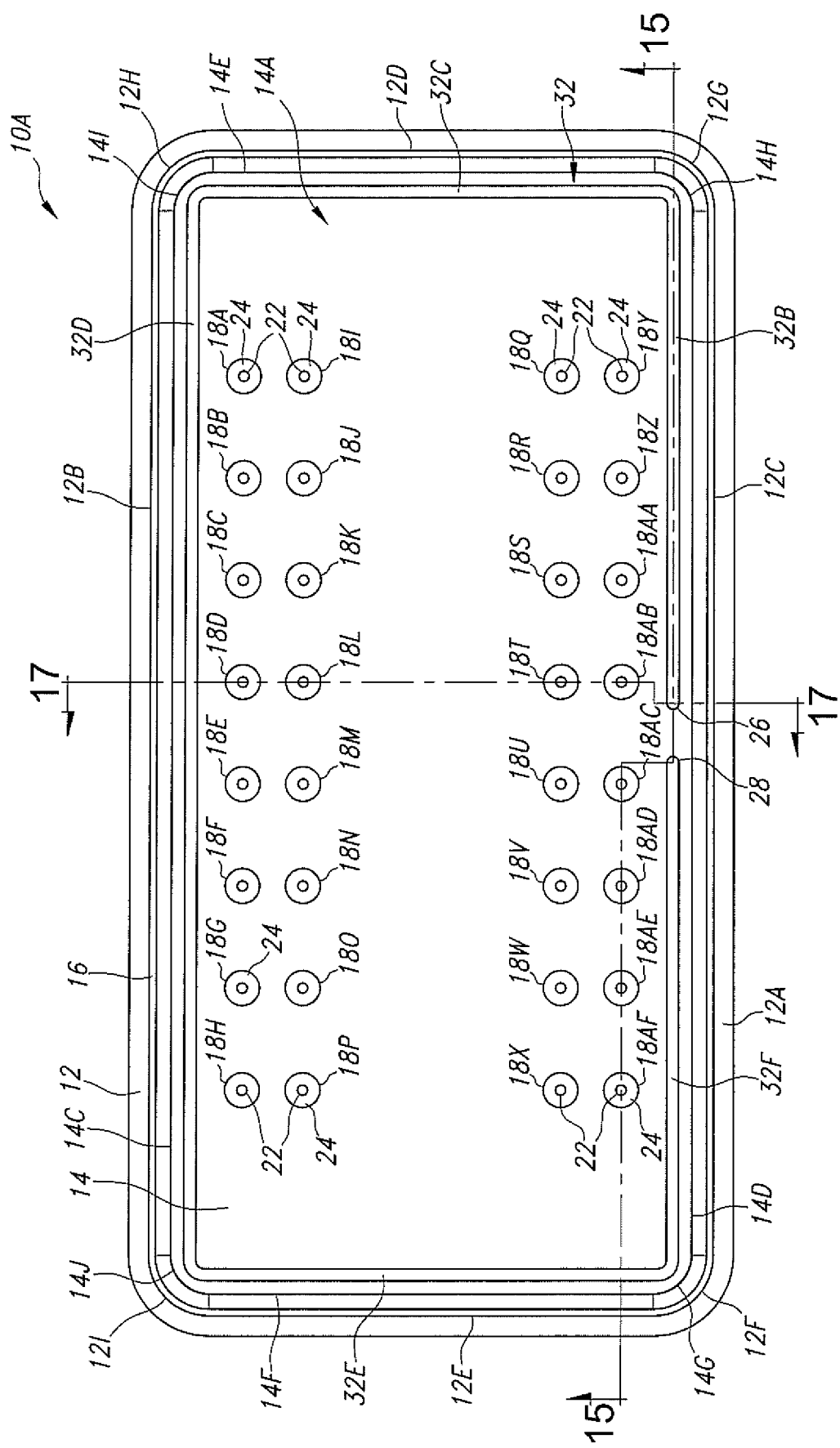
FIG. 12 is a plan view looking at the body fluid side of another embodiment of a feedthrough 10A according to the present invention.
Figure 13:
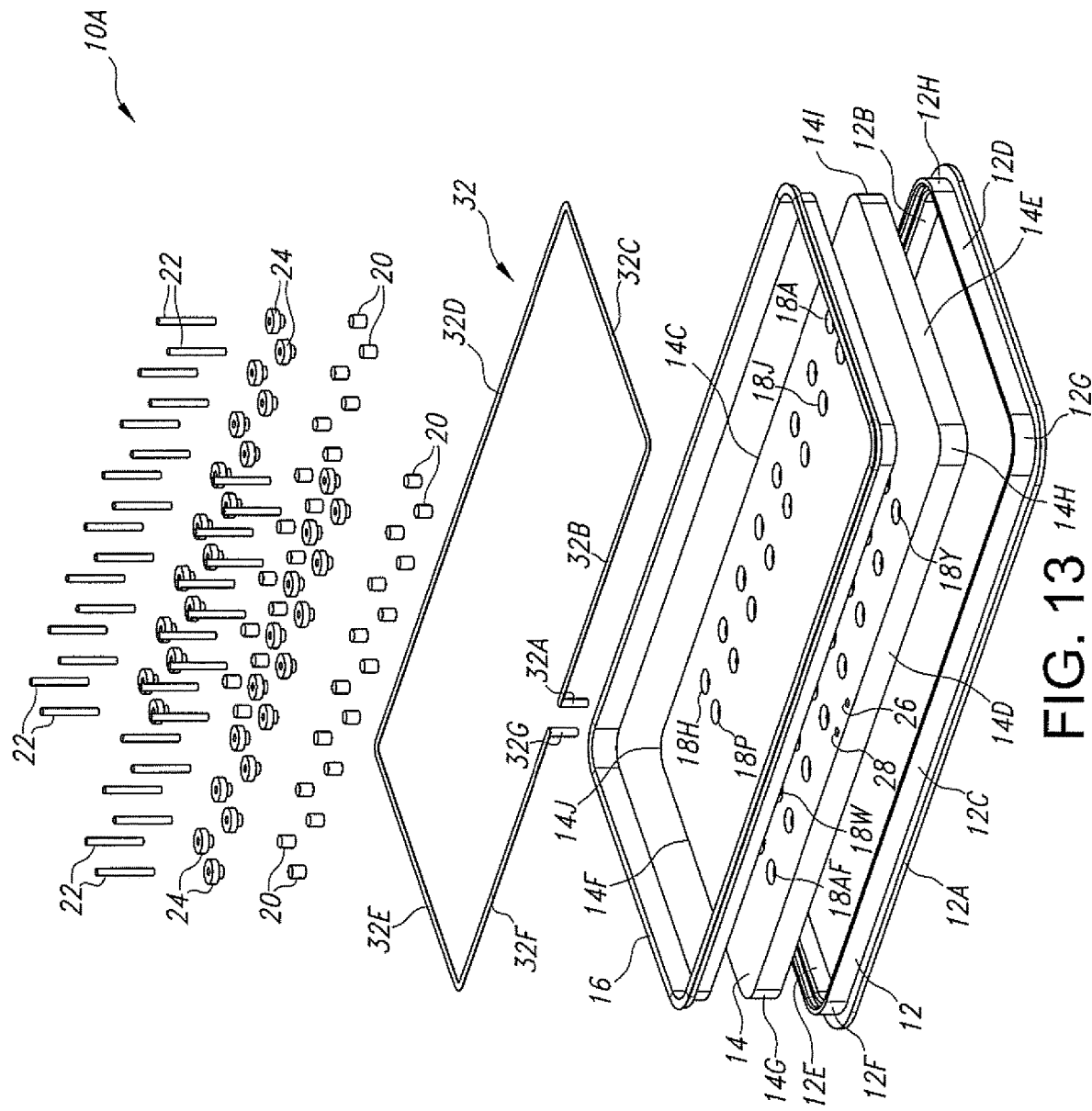
FIG. 13 is an exploded view of the feedthrough 10A shown in FIG. 12.
Figure 18:
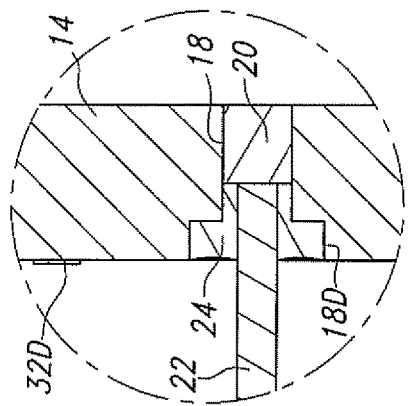
FIG. 18 is an enlarged view of the indicated section of FIG. 17.
Figure 19:
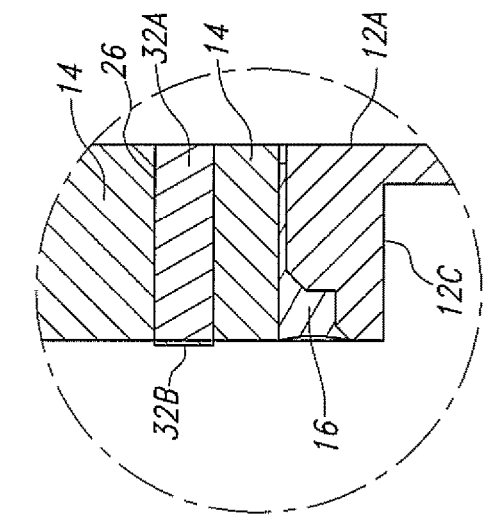
FIG. 19 is an enlarged view of the indicated section of FIG. 17.
Figure 17:
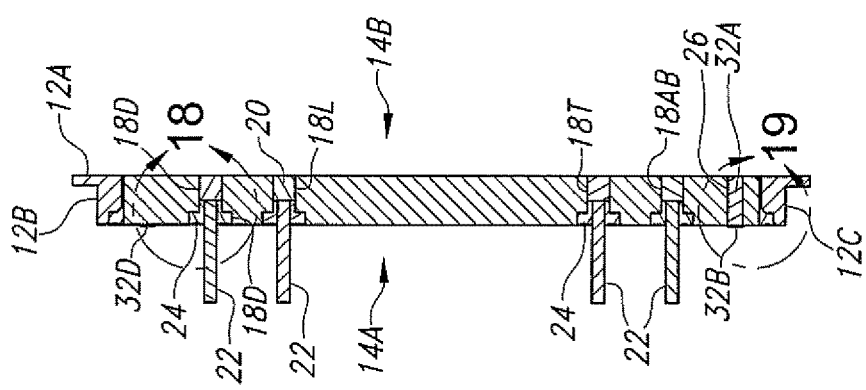
FIG. 17 is a cross-sectional view taken along line 17-17 of FIG. 12.
Figure 20:
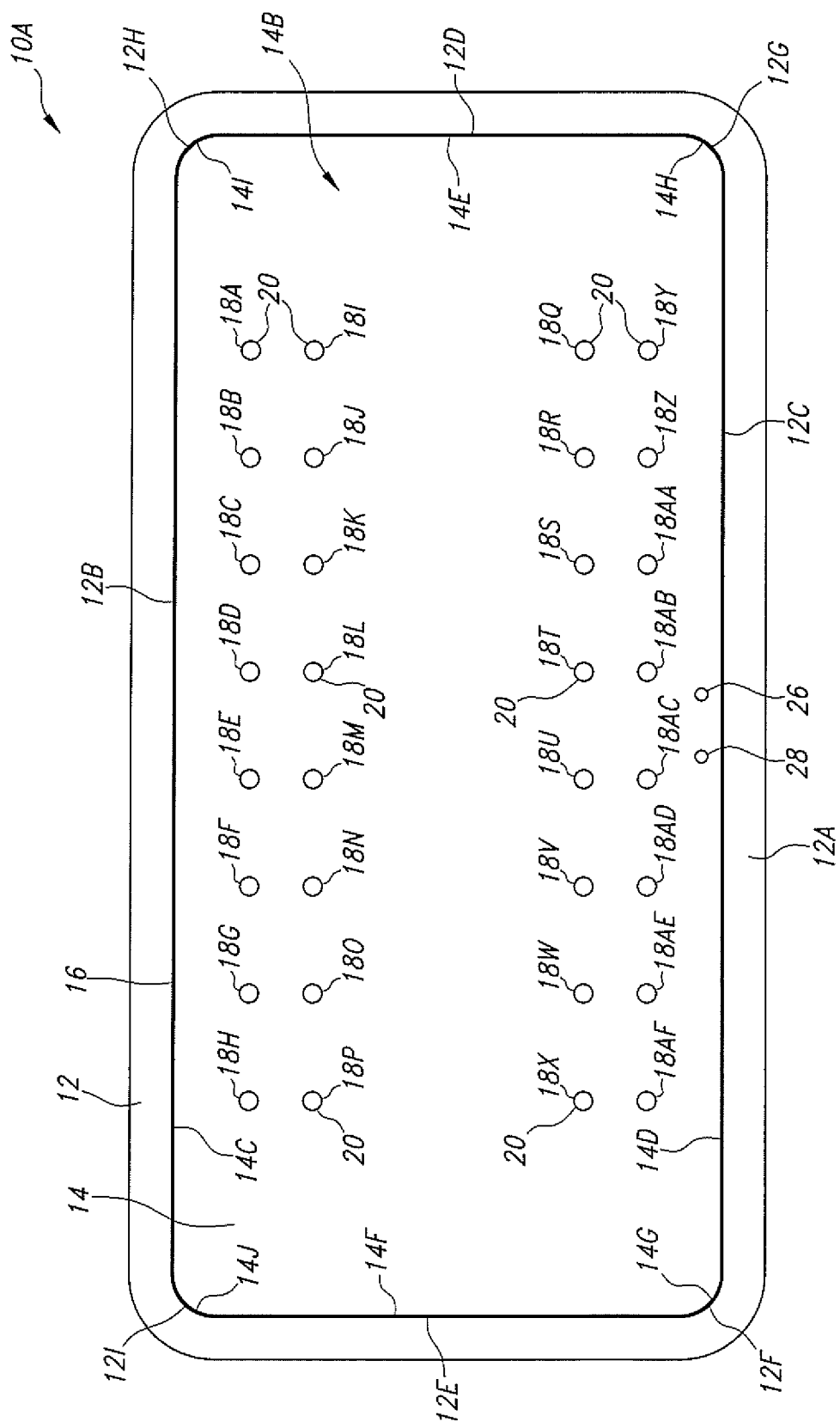
FIG. 20 is a plan view looking at the device side of the feedthrough 10A shown in FIG. 12.

FIGS. 12 to 20 illustrate a second embodiment of a feedthrough 10A according to the present invention. FIGS. 12 and 20 are plan views looking at the body fluid side surface 14A and the device side surface 14B, respectively, of the insulator 14 and FIG. 13 is an exploded view of the feedthrough 10A. Except for the shape of its antenna trace 32, feedthrough 10A has the same structure as the feedthrough 10 shown in FIGS. 3 to 11.

Looking at FIG. 12, in a similar manner as with the antenna trace 30 for feedthrough 10, the electrically conductive trace 32 serving as a charging antenna is supported on the body fluid side surface 14A of the insulator. Since the antenna trace 32 will be exposed to body fluids, and the like, it must be a biocompatible material. Suitable biocompatible materials include platinum, platinum alloys, gold, gold alloys, rhodium, titanium, molybdenum, and mixtures thereof, and the antenna trace 32 may be applied to the insulator by thin and thick film technologies, such as printing, screen printing, pad printing, painting, plating, brush coating, direct bonding, active metal brazing, magnetron sputtering, physical vapor deposition, ion implantation, electroplating, and electroless plating.

The antenna trace 32 has a first leg portion 32A that is received in via 26 where it is hermetically sealed to the insulator. The antenna trace 32 has a first lateral portion 32B that extends along the body fluid side surface 14A between and spaced from the insulator side 14D and the vias 18AB, 18AA, 18Z and 18Y from the first leg portion 32A to a curved turn spaced from the insulator end 14E. There, the first lateral portion 32B of the antenna trace 32 forms a second lateral portion 32C that extends along the body fluid side surface 14A, spaced inwardly from the insulator end 14E. A short distance from insulator side 14C, the antenna trace portion 32C curves toward the insulator end 14F. There, the second lateral portion 32C forms a third lateral portion 32D that extends along the body fluid side surface 14A between and spaced from the first row of vias 18A to 18H and the insulator side 14C and toward the opposite insulator end 14F. Spaced a short distance from the insulator end 14F, the antenna trace portion 32D makes a curved turn and forms a fourth lateral portion 32E that extends along the body fluid side surface 14A. Spaced inwardly from the insulator side 14D, the fourth lateral portion 32E makes another curved turn toward the insulator side 14D. There, the fourth lateral portion 32E forms a fifth lateral portion 32F that extends along the body fluid side surface 14A between but spaced from the vias 18AC to 18AF and the insulator side 14D to meet via 28. At the via 28, the antenna trace 32 forms a second leg portion 32G that resides in the via 28 where it is hermetically sealed to the insulator. The distal ends of the leg portions 32A and 32G reside at the device side surface 14B of the insulator 14 and are configured for subsequent electrical connection to electronic circuits (not shown) housed inside the AIMD 210.

Figure 21:
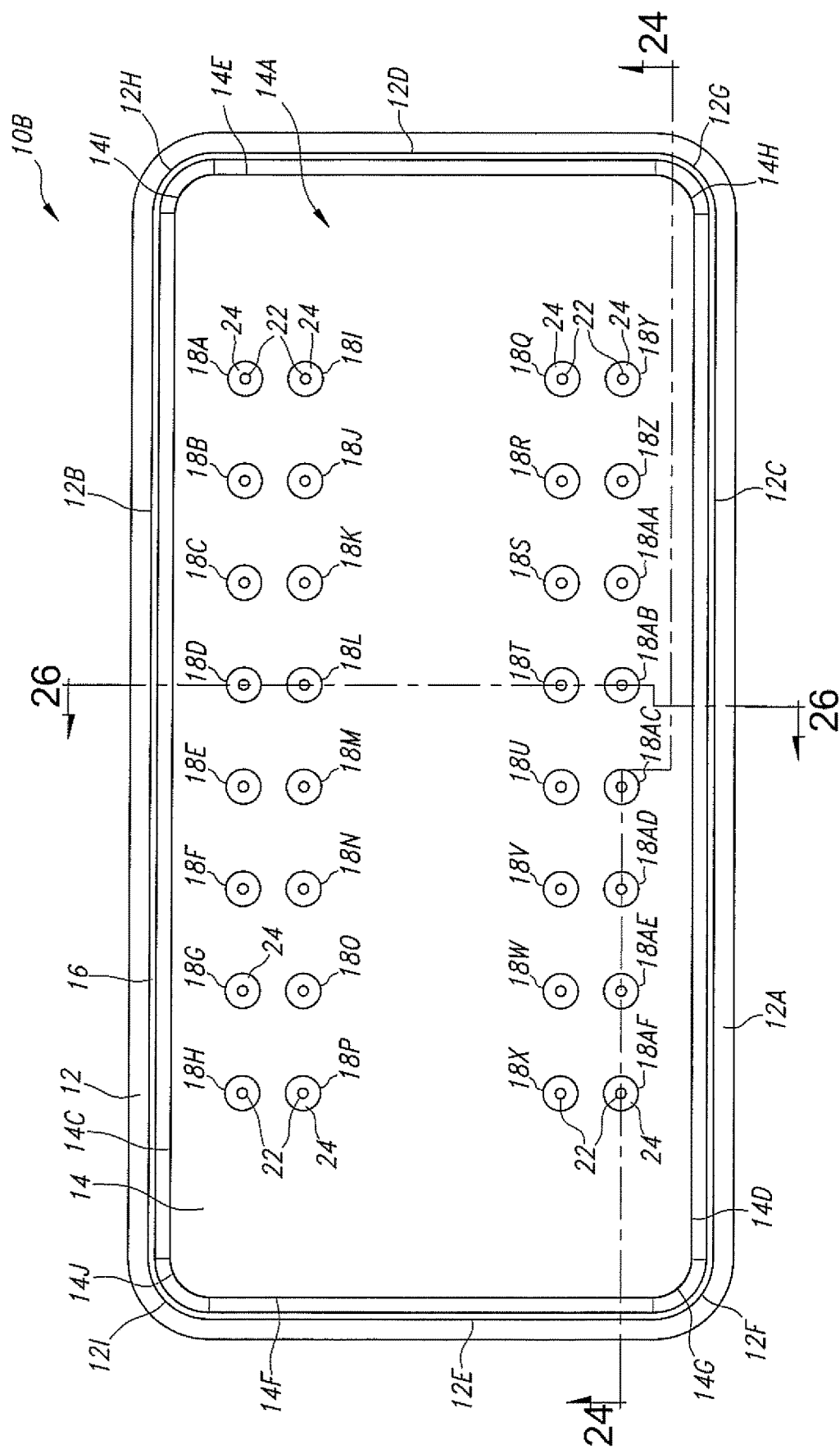
FIG. 21 is a plan view looking at the body fluid side of another embodiment of a feedthrough 10B according to the present invention.
Figure 22:
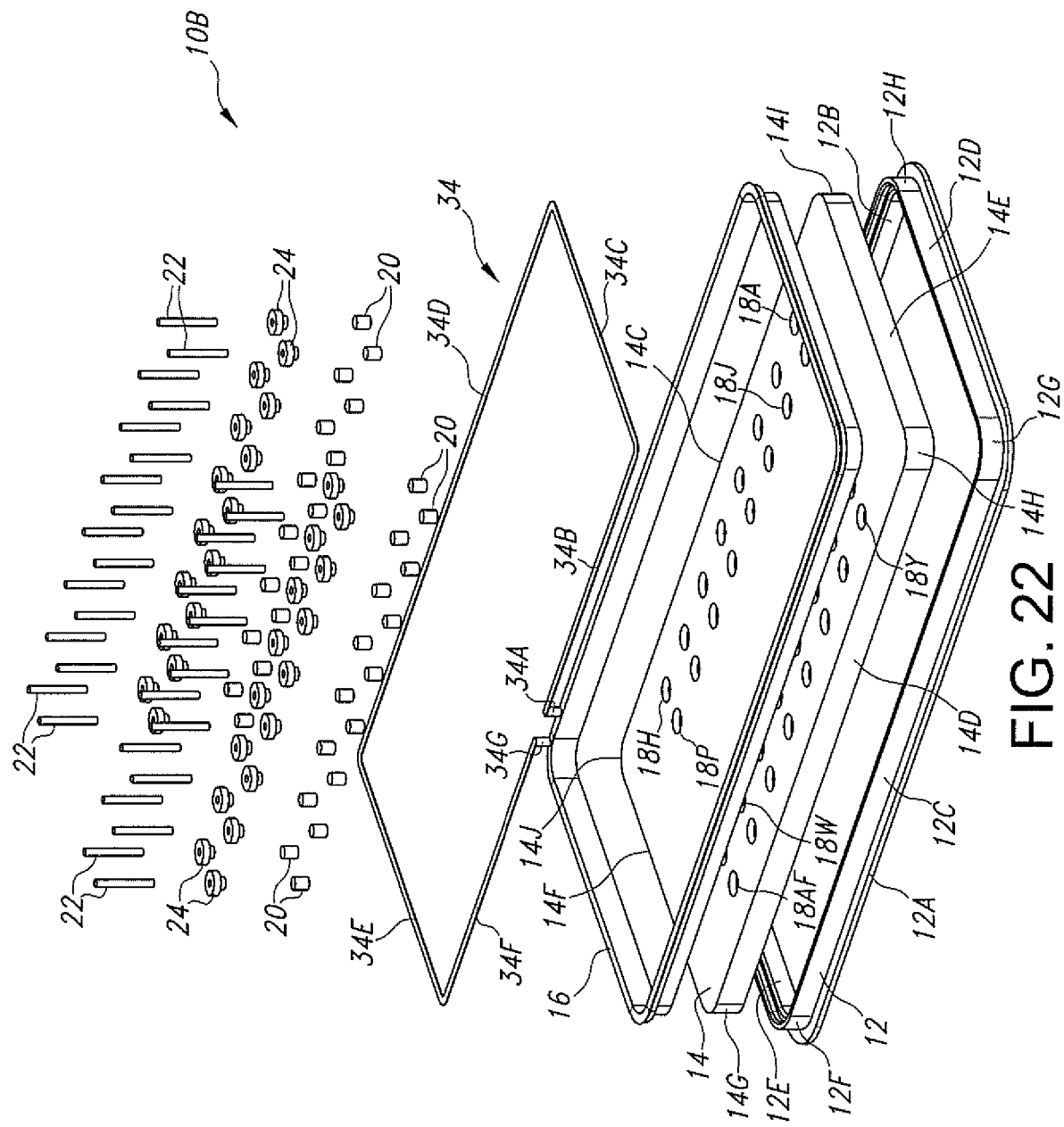
FIG. 22 is an exploded view of the feedthrough 10B shown in FIG. 21.
Figure 29:
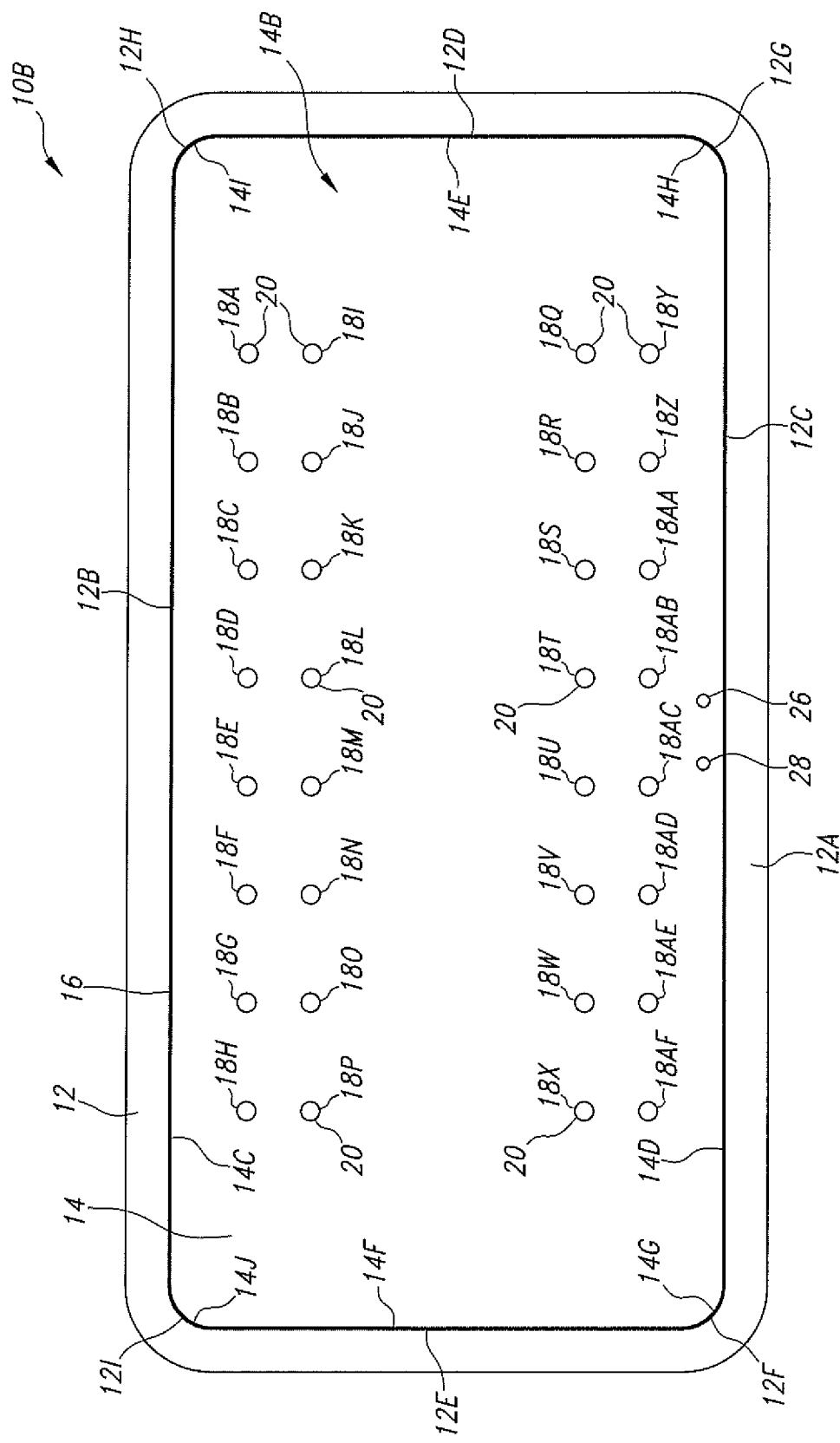
FIG. 29 is a plan view looking at the device side of the feedthrough 10B shown in FIG. 21.

FIGS. 21 to 29 illustrate a third embodiment of a feedthrough 10B according to the present invention. FIGS. 21 and 29 are plan views looking at the body fluid side surface 14A and the device side surface 14B, respectively, of the insulator 14 and FIG. 22 is an exploded view of the feedthrough 10B. Except for the shape and location of its antenna trace 34, feedthrough 10B has the same structure as the feedthrough 10 shown in FIGS. 3 to 11 and the feedthrough 10A shown in FIGS. 12 to 20. While the antenna trace 30 for the feedthrough 10 and the antenna trace 32 for the feedthrough 10A are supported on the body fluid side surface 14A of the insulator 14, the electrically conductive trace 34 serving as a charging antenna can also be embedded inside the insulator, located between the body fluid side and device side surfaces 14A and 14B, respectively. Since the embedded antenna trace 34 will not be exposed to body fluids, and the like, can be of a biocompatible material selected from platinum, platinum alloys, gold, gold alloys, rhodium, titanium, molybdenum, and mixtures thereof, or a material that is not biocompatible selected from copper, copper alloys, platinum, platinum alloys, gold, gold alloys, and mixtures thereof.

In any event, the antenna trace 34 may be applied to a green-state ceramic sheet before the final laminated stack-up thickness is obtained prior to the laminated sheets being subjected to a sintering process. The biocompatible or non-biocompatible material comprising the antenna trace 34 may be deposited by thin and thick film technologies, such as printing, screen printing, pad printing, painting, plating, brush coating, direct bonding, active metal brazing, magnetron sputtering, physical vapor deposition, ion implantation, electroplating, and electroless plating.

The antenna trace 34 has a first leg portion 34A that is received in via 26A where it is hermetically sealed to the insulator 14. The antenna trace 34 has a first lateral portion 34B that extends from the first leg portion 34A between the insulator body fluid and device side surfaces 14A, 14B and spaced from the insulator side 14D and the vias 18AB, 18AA, 18Z and 18Y to a curved turn spaced from the insulator end 14E. There, the first lateral portion 34B of the antenna trace 34 forms a second lateral portion 34C that extends between the insulator body fluid and device side surfaces 14A, 14B, spaced inwardly from the insulator end 14E. A short distance from insulator side 14C, the antenna trace portion 34C curves toward the insulator end 14F. There, the second lateral portion 34C forms a third lateral portion 34D that extends between the insulator body fluid and device side surfaces 14A, 14B and spaced from the first row of vies 18A to 18H and the insulator side 14C toward the opposite insulator end 14F. Spaced a short distance from the insulator end 14F, the antenna trace portion 34D makes a curved turn into a fourth lateral portion 34E that extends between the insulator body fluid and device side surfaces 14A, 14B. Spaced inwardly from the insulator side 14D, the fourth lateral portion 34E makes another curved turn toward the insulator side 14D. There, the fourth lateral portion 34E forms a fifth lateral portion 34F that extends between the insulator body fluid and device side surfaces 14A, 14B and spaced from the vias 18AC to 18AF and the insulator side 14D to meet via 28A. At via 28A, the antenna trace 34 forms a second leg portion 34G that resides in the via 28A where it is hermetically sealed to the insulator 14. The distal ends of the leg portions 34A and 34G reside at the device side surface 14B of the insulator 14 and are configured for subsequent electrical connection to electronic circuits (not shown) housed inside the AIMD 210.

Figure 30:
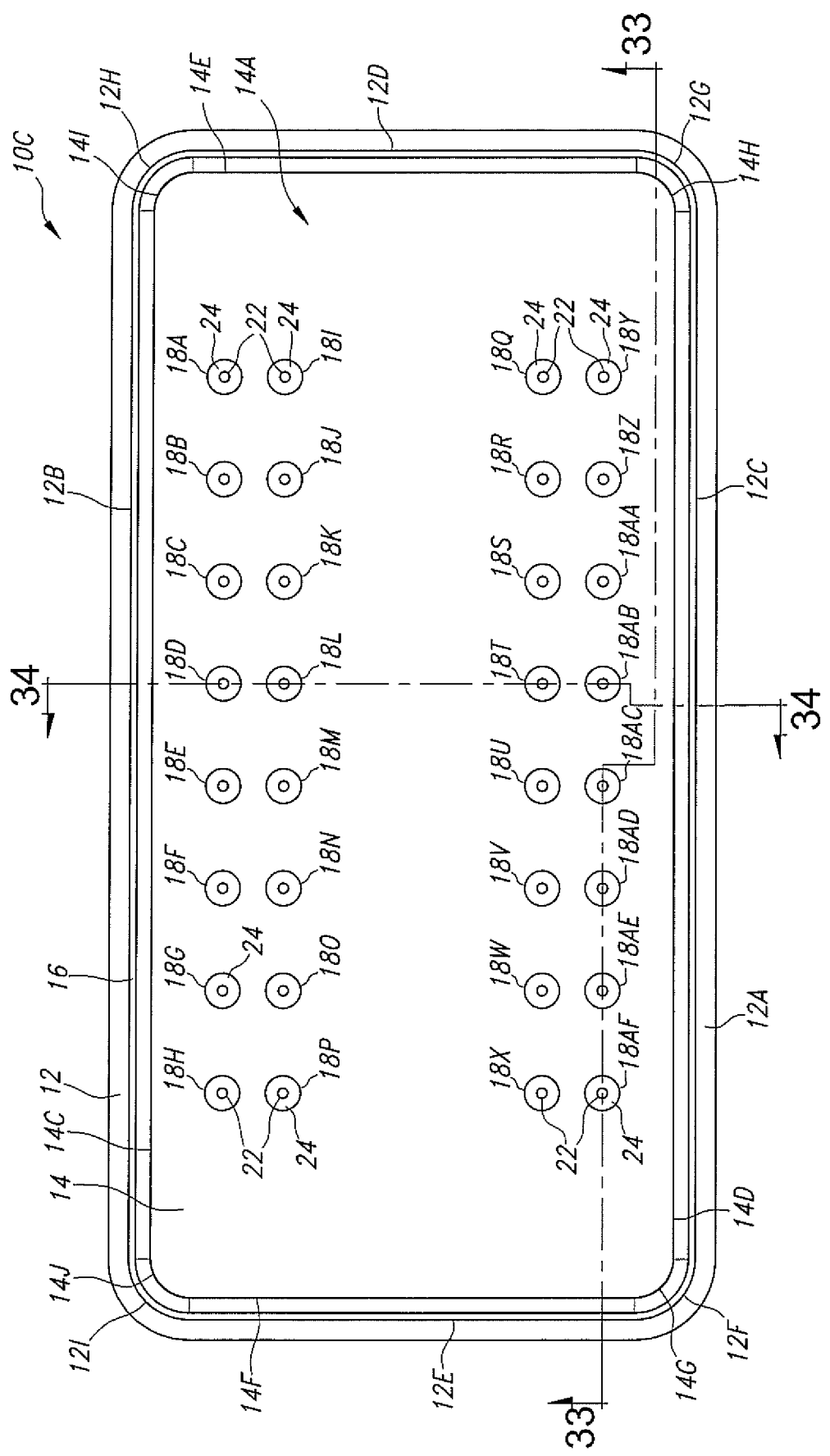
FIG. 30 is a plan view looking at the body fluid side of another embodiment of a feedthrough 10C according to the present invention.
Figure 31:
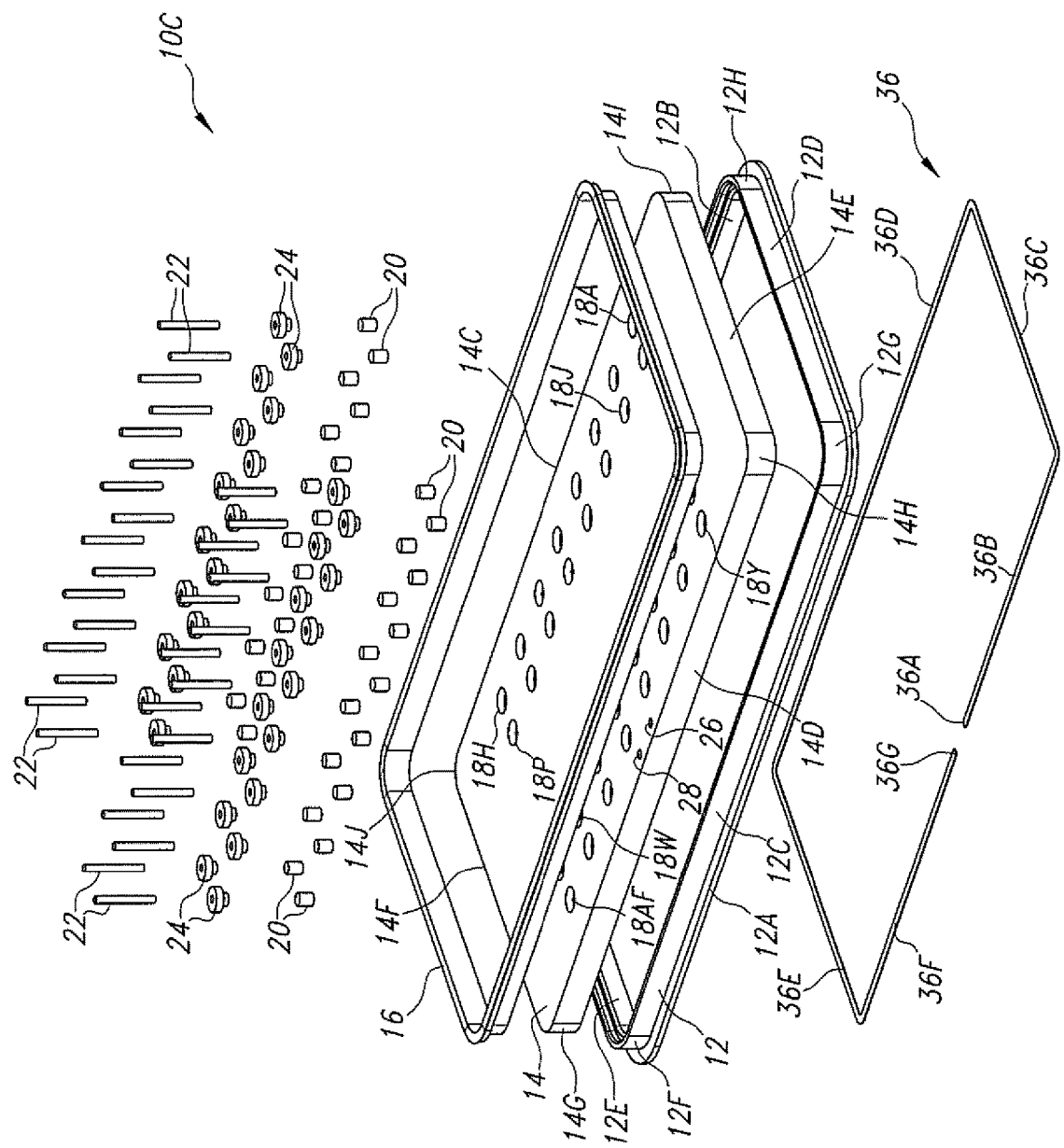
FIG. 31 is an exploded view of the feedthrough 10C shown in FIG. 30.
Figure 35:
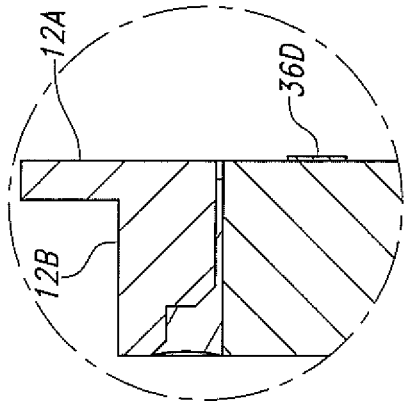
FIG. 35 is an enlarged view of the indicated section of FIG. 34.
Figure 36:
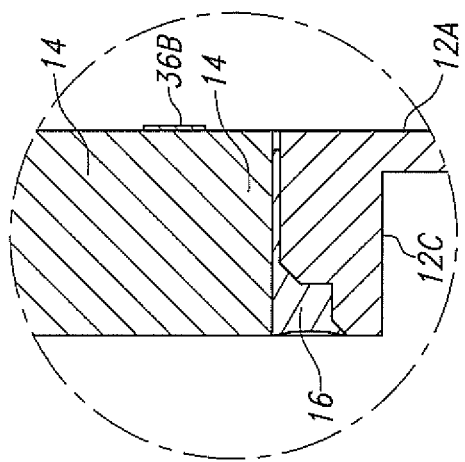
FIG. 36 is an enlarged view of the indicated section of FIG. 34.
Figure 34:
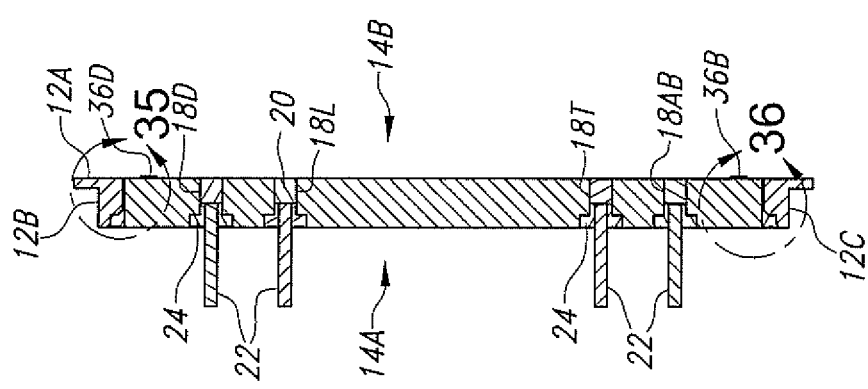
FIG. 34 is a cross-sectional view taken along line 34-34 of FIG. 30.
Figure 37:
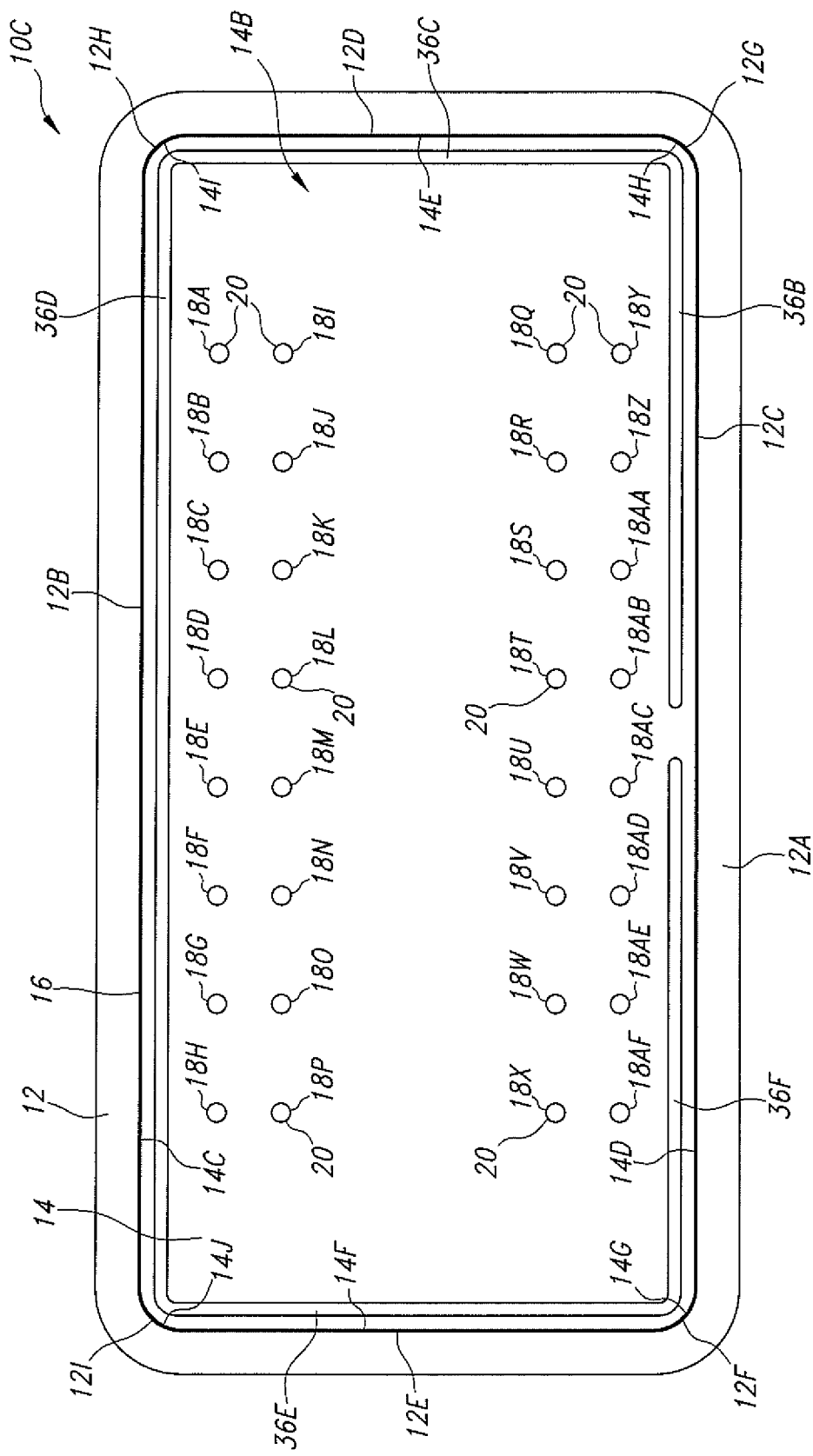
FIG. 37 is a plan view looking at the device side of the feedthrough 100 shown in FIG. 30.

FIGS. 30 to 37 illustrate a fourth embodiment of a feedthrough 10C according to the present invention. FIGS. 30 and 37 are plan views looking at the body fluid side surface 14A and the device side surface 14B, respectively, of the insulator 14 and FIG. 31 is an exploded view of the feedthrough 10C. In this embodiment, the electrically conductive trace 36 serving as a charging antenna is supported on the device side surface 14B of the insulator. This means that there is no need for the vias 26 and 28 shown with respect to the first and second feedthroughs 10A and 10B and the vias 26A and 28A shown for the third feedthrough 10B. Also, since the antenna trace 36 will not be exposed to body fluids, it does not need to be made from a biocompatible material. Suitable material for the antenna trace 36 supported on the device side surface 14B of the insulator include copper, copper alloys, platinum, platinum alloys, gold, gold alloys, and mixtures thereof. Otherwise, the feedthrough 100 has the same structure as the feedthrough 10 shown in FIGS. 3 to 11, the feedthrough 10A shown in FIGS. 12 to 20 and the feedthrough 10B shown in FIGS. 21 to 29.

The antenna trace 36 begins at a first end 36A which is spaced from but adjacent to the via 18AB and the insulator side 14D. From there antenna trace 36 has a first lateral portion 36B that extends along the device side surface 14B between and spaced from the insulator side 14D and the vias 18AB, 18AA, 18Z and 18Y to a curved turn spaced from the insulator end 14E. There, the first lateral portion 36B of the antenna trace 36 forms a second lateral portion 36C that extends along the device side surface 14B, spaced inwardly from the insulator end 14E. A short distance from insulator side 14C, the antenna trace portion 36C curves toward the insulator end 14F. There, the second lateral portion 36C forms a third lateral portion 36D that extends along the device side surface 14B between and spaced from the first row of vias 18A to 18H and the insulator side 14C and toward the opposite insulator end 14F. Spaced a short distance from insulator end 14F, the antenna trace portion 36D makes a curved turn and forms a fourth lateral portion 36E that extends along the device side surface 14A. Spaced inwardly from the insulator side 14D, the fourth lateral portion 36E makes another curved turn and extends toward the insulator side 14D. There, the fourth lateral portion 36E forms a fifth lateral portion 36F that extends along the device side surface 14B between but spaced from the vias 18AC to 18AF and the insulator side 14D to terminate at a second end 36G of the antenna trace 36. The first and second ends 36A and 36G are spaced from but adjacent to each other at the device side surface 14B of the insulator 14 and are configured for subsequent electrical connection to electronic circuits (not shown) housed inside the AIMD 210.

Thus, various embodiments for an inductive charging antenna 30, 32, 34 and 36 supported on or embedded inside the insulator 14 for the feedthrough of a medical device 202 have been described. However, the scope of the present invention charging antennas is not intended to be limited to the specific structures shown in the drawings. For example, while the rectangularly-shaped serpentine portion 30D of the charging antenna 30 in FIGS. 3 to 11 is shown extending between the second and third rows of vias 18I to 18P and 18Q to 18X on the body fluid side surface 14A of the feedthrough insulator 14, that is by way of example only. The same antenna configuration can reside of the device side surface 14B of the insulator or be embedded inside the insulator. Further, the serpentine-shaped portion 30D need not have a rectangular shape. Instead, that portion of the charging antenna trace may have a curved or sinusoidal shape or have several curved or sinusoidal trace sections that are connected to an intermediate lateral trace section. Further, the illustrated feedthroughs 10, 10A, 10B and 10C can have more or less vias than the 32 shown, and the vias need not be aligned in rows of an equal number. Still further, the charging antenna can weave between and among the vias in virtually any pattern that is limited only by the requirements of the medical device into which the feedthrough will be built. Moreover, feedthrough embodiments 10A and 10C can encircle or surround any number of feedthrough vias or, regardless the number of vias, the charging antenna can surround the feedthrough vias as an embedded antenna disposed between the body fluid and device side surfaces of the insulator 14.

Referring back to FIG. 2, with the medical device 202, for example, the AIMD 210 implanted in body tissue, the external charger 204 of the medical device system 200 is configured to provide inductive charging current to the various charging antennas 30, 32, 34 and 36. The charging antennas are connected to electronic circuits housed inside the medical device 202. In addition to controlling the delivery of electrical stimulation to a patient and to receiving sensed biological signals from body tissue, the electronic circuits control inductive charging of the battery or capacitor power source (not shown) that provides electrical power for those functionalities, among others. The electrical energy power source can be a capacitor or a rechargeable battery, for example, a hermetically sealed rechargeable Li-ion battery. An exemplary rechargeable electrical energy power source is a lithium-ion electrochemical cell comprising a carbon-based or $Li_4Ti_5O_{12}$-based anode and a lithium metal oxide-based cathode, such as of $LiCoO_2$ or lithium nickel manganese cobalt oxide ($LiNi_aMn_bCo_{1-a-b}O_2$).

Inductive charging power may be delivered to the charging antennas 30, 32, 34 and 36 from an external charging pad 216 containing a transmitting coil (not shown) connected to the external charger 204. In some embodiments, the external charging pad 216 is a hand-held device that is connected to the external charger 204 by a multiconductor cable which includes (power conductors and control lines). In another embodiment, the external charging pad 216 is an internal component of the external charger 204.

It is appreciated that various modifications to the inventive concepts described herein may be apparent to those skilled in the art without departing from the spirit and scope of the present invention as defined by the hereinafter appended claims.

What is claimed is:

1. A feedthrough, comprising:
   a) an electrically conductive ferrule comprising a a) ferrule sidewall defining a ferrule opening, the ferrule sidewall extending to a ferrule body fluid side and a ferrule device side;
   b) a ceramic insulator hermetically sealed to the ferrule in the ferrule opening, the ceramic insulator extending to an insulator body fluid side surface at or adjacent to the ferrule body fluid side and an insulator device side surface at or adjacent to the ferrule device side;
   at least a first electrically conductive pathway extending through the ceramic insulator to the insulator body fluid and device side surfaces; and
   d) at least one electrically conductive antenna trace comprising at least one of:
      A) a body fluid side length supported entirely on the insulator body fluid side surface and extending from a first conductive leg extending through the ceramic insulator to a second conductive leg extending through the ceramic insulator, wherein the first and second conductive legs have respective first and second conductive leg ends residing at the insulator device side surface, the first and second conductive leg ends being configured for subsequent electrical connection to at least one electronic circuit; and
      B) a device side length supported entirely on the insulator device side surface and extending to first and second conductive trace ends at the insulator device side surface, the first and second conductive trace ends of the device side length of the electrically conductive antenna trace being configured for subsequent electrical connection to at least one electronic circuit.

2. The feedthrough of claim 1, wherein a second electrically conductive pathway extends through the ceramic insulator to the insulator body fluid and device side surfaces.

3. The feedthrough of claim 2, wherein the at least one electrically conductive antenna trace either surrounds the first and second conductive pathways or extends between but does not contact the first and second conductive pathways.

4. The feedthrough of claim 2, wherein there is at least two rows of electrically conductive pathways extending through the ceramic insulator to the insulator body fluid and device side surfaces, and wherein the at least one electrically conductive antenna trace extends between but does not contact the at least two rows of electrically conductive pathways.

5. The feedthrough of claim 1, wherein, if the electrically conductive antenna trace is supported entirely on the insulator body fluid side surface, it is selected from platinum, platinum alloys, gold, gold alloys, rhodium, titanium, molybdenum, and mixtures thereof.

6. The feedthrough of claim 1, wherein, if the electrically conductive antenna trace is supported entirely on the insulator device side surface, it is selected from platinum, platinum alloys, gold, gold alloys, rhodium, titanium, molybdenum, copper, copper alloys, and mixtures thereof.

7. The feedthrough of claim 1, wherein the at least one electrically conductive antenna trace is contacted to at least one of the insulator body fluid side surface and the insulator device side surface by at least one of printing, screen printing, pad printing, painting, plating, brush coating, direct bonding, active metal brazing, magnetron sputtering, physical vapor deposition, ion implantation, electroplating, and electroless plating.

8. The feedthrough of claim 1, wherein the ceramic insulator is selected from alumina, 3% YSZ, zirconia, sapphire, aluminum nitride, alumina toughened zirconia, boron nitride, ceramic-on-ceramic, partially stabilized zirconia, strontium aluminate, yttria-stabilized zirconia, zirconia toughened alumina, zirconia toughened ceramics, celsian ($BaAl_2Si_2O_8$), a $Li_2O \times Al_2O_3 \times nSiO_2$ glass-ceramic system (LAS system), a $MgO \times Al_2O_3 \times nSiO_2$ glass-ceramic system (MAS system), a $ZnO \times Al_2O_3 \times nSiO_2$ glass-ceramic system (ZAS system), and combinations thereof.

9. The feedthrough of claim 1, wherein the ceramic insulator is characterized as having been sintered from a unitary body of green-state ceramic material or is characterized as having been sintered from a plurality of green-state ceramic sheets stacked one upon another.

10. The feedthrough of claim 1, wherein the first electrically conductive pathway comprises a device side first conductive pathway portion of a first diameter that extends from the insulator device side surface to an annular step in the insulator that widens to a body fluid side first conductive pathway portion extending to the insulator body fluid side surface, the body fluid side first conductive pathway portion having a second diameter that is greater than the first diameter, and wherein the device side first conductive pathway portion comprises a platinum-containing material that is characterized as having been co-sintered with the ceramic insulator, and the body fluid side first conductive pathway portion comprises a terminal pin that is hermetically brazed to the ceramic insulator, and wherein the terminal pin abuts the platinum-containing material to form the first electrically conductive pathway extending from the insulator body fluid side surface to the insulator device side surface.

11. The feedthrough of claim 1, wherein the at least one electrically conductive antenna trace has a rectangularly-shaped serpentine trace portion, or a sinusoidal trace portion that is supported entirely on the insulator body fluid side surface except for the first and second conductive legs or that is supported entirely on the insulator device side surface.

12. A feedthrough, comprising:
a) an electrically conductive ferrule comprising a ferrule sidewall defining a ferrule opening, the ferrule sidewall extending to a ferrule body fluid side and a ferrule device side;
b) an alumina insulator hermetically sealed to the ferrule in the ferrule opening, the alumina insulator extending to an insulator body fluid side surface at or adjacent to the ferrule body fluid side and an insulator device side surface at or adjacent to the ferrule device side;
at least a first platinum-containing conductive pathway and a second platinum-containing conductive pathway extending through the alumina insulator to the insulator body fluid and device side surfaces; and
d) at least one electrically conductive antenna trace comprising at least one of:
A) a body fluid side length supported entirely on the insulator body fluid side surface and extending from a first conductive leg extending through the alumina insulator to a second conductive leg extending through the alumina insulator, wherein the first and second conductive legs have respective first and second conductive leg ends residing at the insulator device side surface, the first and second conductive leg ends being configured for subsequent electrical connection to at least one electronic circuit; and
B) a device side length supported entirely on the insulator device side surface and extending to first and second conductive trace ends at the insulator device side surface, the first and second conductive trace ends of the device side length of the electrically conductive antenna trace being configured for subsequent electrical connection to at least one electronic circuit.

13. The feedthrough of claim 12, wherein the at least one electrically conductive antenna trace either surrounds the first and second conductive pathways or extends between but does not contact the first and second conductive pathways.

14. The feedthrough of claim 12, wherein, if the at least one electrically conductive antenna trace is supported entirely on the insulator body fluid side surface, it is selected from platinum, platinum alloys, gold, gold alloys, rhodium, titanium, molybdenum, and mixtures thereof, and wherein, if the at least one electrically conductive antenna trace is supported entirely on the insulator device side surface, it is selected from platinum, platinum alloys, gold, gold alloys, rhodium, titanium, molybdenum, copper, copper alloys, and mixtures thereof.

15. The feedthrough of claim 12, wherein the at least one electrically conductive antenna trace is contacted to the alumina insulator by at least one of printing, screen printing, pad printing, painting, plating, brush coating, direct bonding, active metal brazing, magnetron sputtering, physical vapor deposition, ion implantation, electroplating, and electroless plating.

16. The feedthrough of claim 12, wherein the alumina insulator is characterized as having been sintered from a unitary body of green-state alumina material or sintered from a plurality of green-state alumina sheets stacked one upon another.

17. The feedthrough of claim 12, wherein at least one of the first and second conductive pathways comprises a device side conductive pathway portion of a first diameter that extends from the insulator device side surface to an annular step in the insulator that widens to a body fluid side conductive pathway portion extending to the insulator body fluid side surface, the body fluid side conductive pathway portion having a second diameter that is greater than the first diameter, and wherein the device side conductive pathway portion comprises a platinum-containing material that is characterized as having been co-sintered with the alumina insulator, and the body fluid side conductive pathway portion comprises a terminal pin that is hermetically brazed to the alumina insulator, and wherein the terminal pin abuts the platinum-containing material to form at least one of the first and second platinum-containing conductive pathways extending from the insulator body fluid side surface to the insulator device side surface.

18. The feedthrough of claim 12, wherein there is at least two rows of conductive pathways extending through the alumina insulator to the insulator body fluid and device side surfaces, each row of conductive pathways comprising at least two conductive pathways, and wherein the at least one electrically conductive antenna trace extends between but does not contact the at least two rows of conductive pathways.

19. The feedthrough of claim 12, wherein the at least one electrically conductive antenna trace has a rectangularly-shaped serpentine trace portion, or a sinusoidal trace portion that is supported entirely on the insulator body fluid side surface except for the first and second conductive legs or that is supported entirely on the insulator device side surface.

20. A hermetic seal, comprising:
a) an electrically conductive ferrule comprising a ferrule sidewall defining a ferrule opening, the ferrule sidewall extending to a ferrule body fluid side and a ferrule device side;
b) a ceramic insulator hermetically sealed to the ferrule in the ferrule opening, the ceramic insulator extending to an insulator body fluid side surface at or adjacent to the ferrule body fluid side surface and an insulator device side surface at or adjacent to the ferrule device side surface; and
c) at least one electrically conductive antenna trace comprising at least one of:
A) a body fluid side length supported entirely on the insulator body fluid side surface and extending from a first conductive leg extending through the ceramic insulator to a second leg extending through the ceramic insulator, wherein the first and second conductive legs have respective first and second conductive leg ends residing at the insulator device side surface, the first and second conductive leg ends being configured for subsequent electrical connection to at least one electronic circuit; and
B) a device side length supported entirely on the insulator device side surface and extending to first and second conductive trace ends at the insulator device side surface, wherein the first and second conductive trace ends are configured for subsequent electrical connection to at least one electronic circuit.

* * * * *